United States Patent [19]

Elliott

[11] Patent Number: 5,398,183

[45] Date of Patent: Mar. 14, 1995

[54] HOLTER ECG REPORT GENERATING SYSTEM

[75] Inventor: Gordon L. Elliott, Kansas City, Mo.

[73] Assignee: Biomedical Systems Corporation, St. Louis, Mo.

[21] Appl. No.: 624,746

[22] Filed: Dec. 10, 1990

[51] Int. Cl.⁶ .................... G06F 15/00; A61B 5/04
[52] U.S. Cl. .................. 364/413.06; 128/702
[58] Field of Search ................. 364/413.06; 128/702–706; 341/138–141, 106

[56] References Cited

U.S. PATENT DOCUMENTS

| | | | |
|---|---|---|---|
| 4,933,675 | 6/1990 | Beard | 341/140 |
| 4,947,858 | 8/1990 | Smith | 128/696 |
| 4,951,680 | 8/1990 | Kird et al. | 128/702 |
| 5,092,340 | 3/1992 | Yamaguchi et al. | 364/413.06 |

Primary Examiner—Donald E. McElheny, Jr.
Assistant Examiner—X. M. Chung-Trans
Attorney, Agent, or Firm—Senniger, Powers, Leavitt & Roedel

[57] ABSTRACT

A system used by a technician for evaluating a Holter ECG tape having a signal representing a series of waveforms thereon and for generating a report reflecting the evaluation. A tape reader generates from the ECG tape an analog signal representative of the ECG waveforms recorded on the tape. An A/D converter converts the analog signal into a digital signal. A computer including a data bus, a memory, a processor controls the operation of the system. A display displays waveforms representing the ECG. A storage device is connected to the data bus. A direct memory access device moves the digital signals from the converter to the memory for storing the digital signal in the storage device. The converter provides at least a 12 bit a digital signal corresponding to the analog signal and includes means for converting the 12 bit digital signal to an 8 bit digital signal.

25 Claims, 7 Drawing Sheets

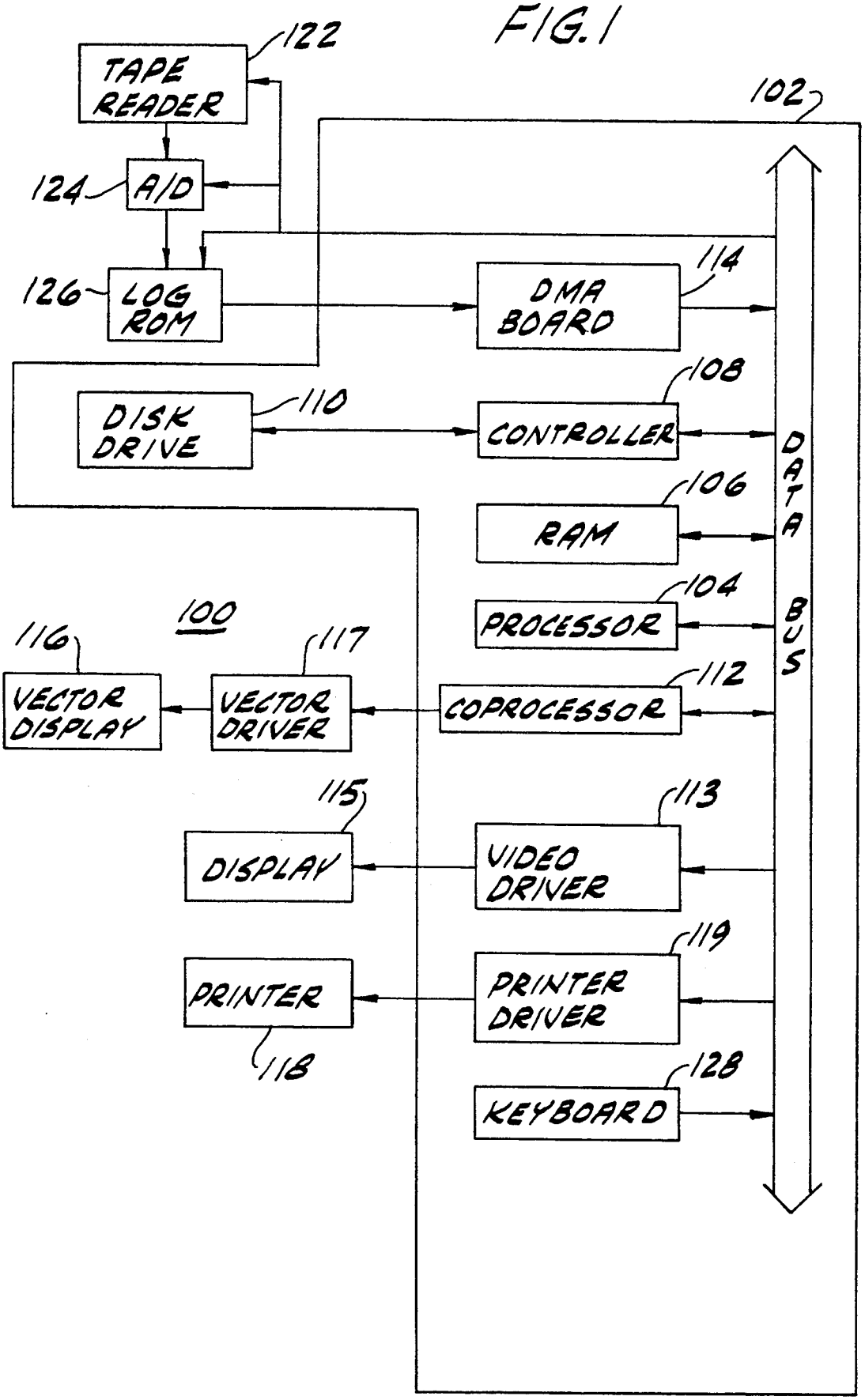

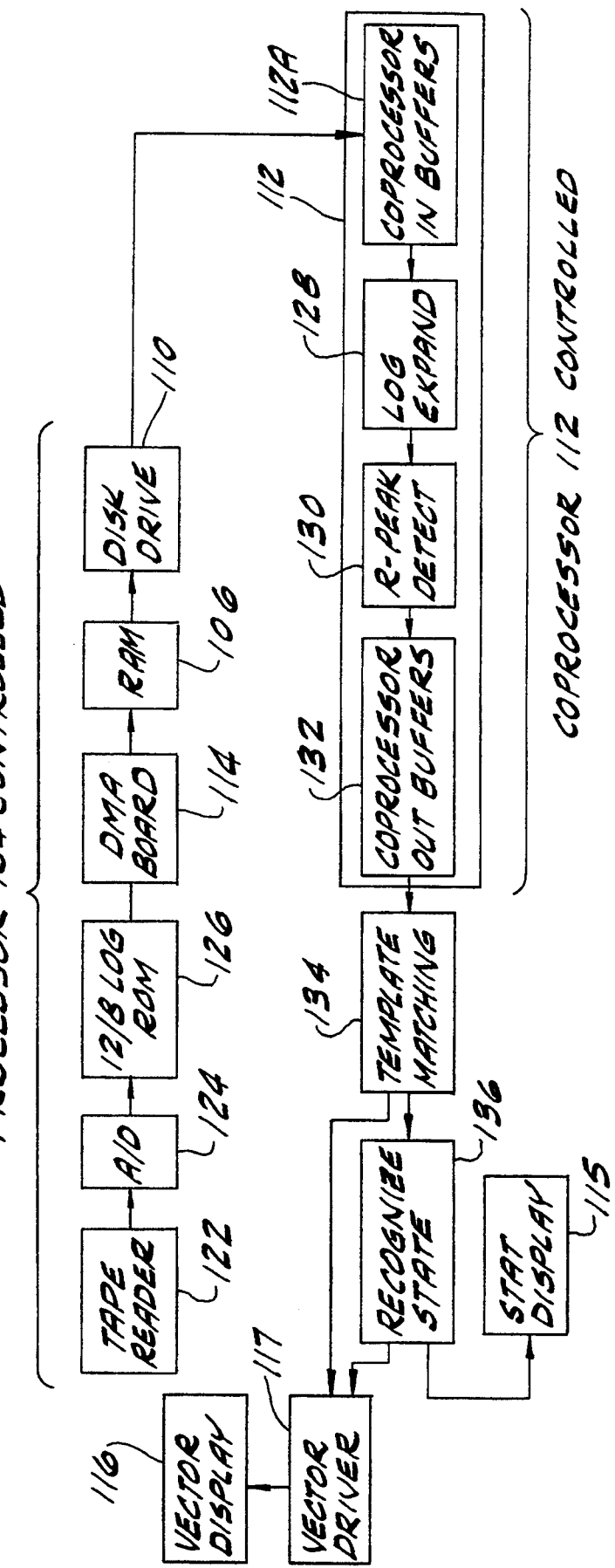

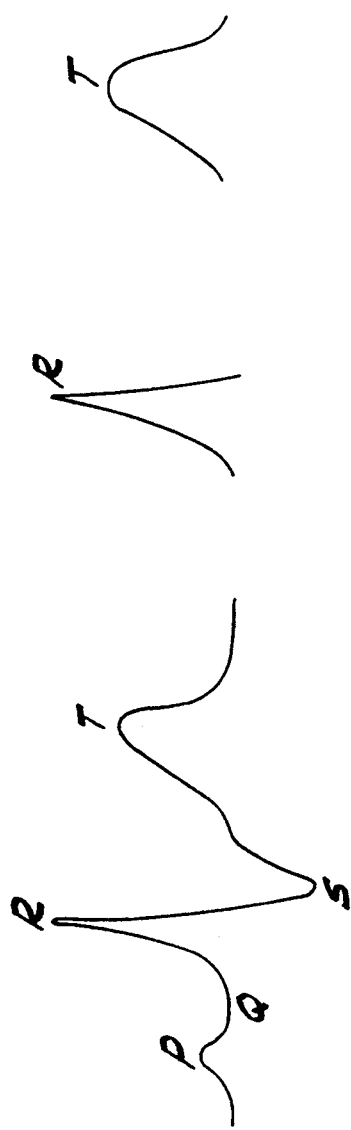
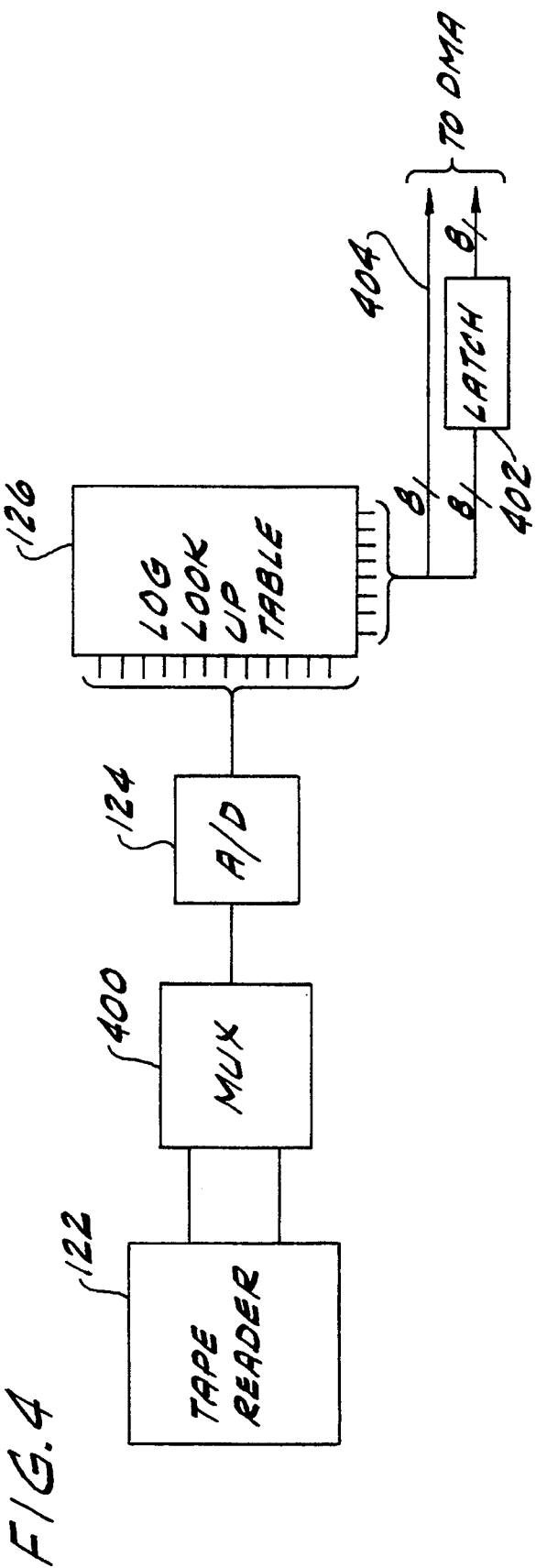

FIG. 6

```
                          BIGEMINY          VE PAIR   VTACH    SINGLE
EXAMPLE                                                         VE    EXAMPLE
         1  2  3  4  5  6  7  8  9 10 11 12 13 14 15 16 17 18 19 20
         N  N  V  N  V  N  V  N  V  N  V  V  N  V  V  V  N  V  N  N
             S3   S5   S7   S9      S11   S14      S18
             VE   VE   VE   VE      VE    VE       VE
              *    *    *    *       **    **       *
S1  A-x. END                              S12     S15 S16
S2    . A--B--C--F--G--H--I--J--I--J-x.
             *     *     *     *    S2"
                                 -K-x. -K--BIGEMINY (4 BEATS)
                            SET BF  S2'
                                         · CLEAR BF
S4  . . . A--B--C--F--G-x.
             *     *
S6  . . . . . A--B--C--F--G-x.
                 *     *
S8  . . . . . . . A--B--C--F-x.
                     *     *
S10 . . . . . . . . . A--B--D--V PAIR.
                         *  *
                                                   (3 BEATS)
S13 . . . . . . . . . . . . A--B--D--E--VTACH.
                               *  *  *
S17 . . . . . . . . . . . . . . . . A--B--C-x.
                                       *
S19 . . . . . . . . . . . . . . . . . . . A--x
S20 . . . . . . . . . . . . . . . . . . . . A
```

HOLTER ECG REPORT GENERATING SYSTEM

BACKGROUND OF THE INVENTION

The invention generally relates to ECG evaluating systems and, in particular, a system for evaluating a Holter ECG and for generating a report of the evaluation.

Holter ECG evaluating systems are well known such as disclosed in U.S. Pat. Nos. 4,183,354, 4,211,238, 4,316,249, 4,333,475, 4,336,810, 4,633,881 and 4,667,682, incorporated herein by reference. However, these systems have various drawbacks which make them slow and/or inaccurate.

SUMMARY OF THE INVENTION

It is an object of this invention to provide an ECG evaluating system which is software based employing off the shelf hardware components.

It is an object of this invention to provide an ECG evaluating system which provide interactive superimposition so that every beat is superimposed on normal beats.

It is an object of this invention to provide an ECG evaluating system which simultaneously analyzes two channels so that arrhythmias that show up in in only one channel can be detected.

It is an object of this invention to provide an ECG evaluating system which employs at least 200 templates.

It is an object of this invention to provide an ECG evaluating system which scans the ECG tape independently of operator interaction and analysis by picking out waveforms in the background while a second processor performs template matching and other analysis and displays superimposed waveforms for the operator.

It is an object of this invention to provide an ECG evaluating system which provides artifact rejection while retaining for analysis beats which match known templates.

It is an object of this invention to provide an ECG evaluating system which employs nondeterministic state analysis.

The system according to the invention is used by a technician for evaluating a Holter ECG tape having a signal representing a series of waveforms thereon and for generating a report reflecting the evaluation. Means generates from the ECG tape an analog signal representative of the ECG waveforms recorded on the tape. Means converts the analog signal into a digital signal. Computing means including a data bus, a memory, a processor controls the operation of the system. Means displays waveforms representing the ECG. A storage device is connected to the data bus. Direct memory access means moves the digital signals from the converting means to the memory for storing the digital signal in the storage device. The means for converting provides at least 12 a bit digital signal corresponding to the analog signal and includes means for converting the 12 bit digital signal to an 8 bit digital signal.

Other objects and features will be in part apparent and in part pointed out hereinafter.

BRIEF DESCRIPTION OF THE DRAWINGS

FIG. 1 is a block diagram of a Holter ECG report generating system according to the invention.

FIG. 2 is a diagram of the data flow according to the invention.

FIG. 3A is a waveform diagram of an ECG wave.

FIG. 3B is a waveform diagram of an R wave template.

FIG. 3C is a waveform diagram of a T wave template.

FIG. 4 a block diagram of a ROM having a 12-bit input and an 8-bit output generated by a LOG look-up table therein.

FIG. 6 is a state sequencing diagram for a 20 beat example analyzed according to the nondeterministic state diagram of FIG. 5.

Figure 5:
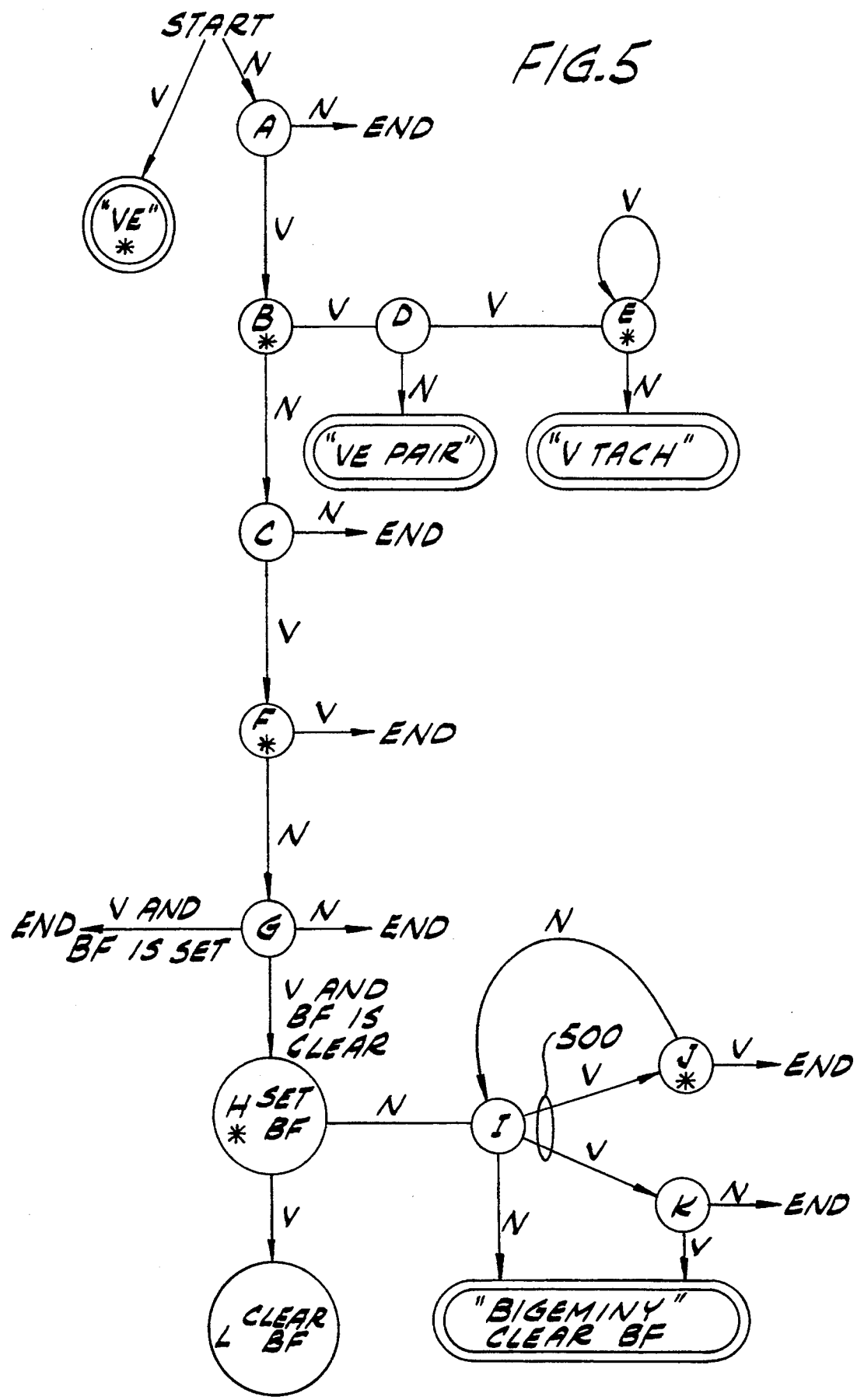
FIG. 5 is nondeterministic state diagram.

Appendix A is a description of each of the software programs for implementing the system according to the invention.

Corresponding reference characters indicate corresponding parts throughout the several views of the drawings.

DETAILED DESCRIPTION OF PREFERRED EMBODIMENTS

The system of the invention is an electrocardiogram analyst's tool for analyzing electrocardiogram magnetic tapes recorded by Holter-type monitors. The system has been designed to meet the highest standards of Holter analysis by superimposition. The system was designed with accuracy and speed being its topmost objectives. A secondary, but also important consideration has been to design the system with "off the shelf" components, and this has been accomplished with today's technological advancements like the Intel 80386, and fast access disk controllers. This design objective was adopted so that systems used in the field could be serviced with minimum technical expertise.

FIG. 1 illustrates the processing hardware. The system 100 comprises an IBM compatible microcomputer 102 with an Intel 80386 microprocessor 104. It has two (2) Megabytes of RAM 106, a RAM cache disk controller 108 with an average access time of under 1.0 msec. with a standard hard disk drive 110 such as a Seagate ST250 80 Megabyte hard disk drive. A second on-board computer is used to perform high speed analysis and calculations; this is a SC/FOX coprocessor board 112 from Silicon Composers, Inc. The board uses a Harris RTX-2000 microprocessor, which is a 16-bit stack oriented processor that implements the FORTH language almost directly. The processor runs at about 8 to 10 million instructions per second according to Silicon Composers, Inc. specifications. A direct memory access (DMA) board 114 is used to transfer an analog to digital (A/D) and digital to analog (D/A) conversion data. For example, the DMA board 114 may be a PDMA-32 from Metrabyte Corporation, which allows the external A/D conversions to make use of the on-board DMA chip to make direct memory transfers without the aid of the Intel 80386 processor 104.

The main processor 104 performs both the task of reading the data from the a/d converter 124 and the task of processing the template match 134 and displaying the results, by a form of simple multi-tasking. The data is moved from the a/d converter 124 by the DMA hardware 114. This allows each 16 bit word (two 8 bit log compressed samples) to be moved to RAM when the data word is ready, without interrupting the main processor 104 (except for the length of a single DMA to memory cycle). The data accumulates in a buffer of RAM 106. The main processor's algorithm must periodically check whether the buffer is full enough to move the data to disk 110. This is done by processing one beat, then checking the various buffers or tasks. The main processor 104 also similarly checks if the co-processor's input buffers 112*a* need filling in a similar manner.

In one preferred embodiment of the system 100, a vector display scope was attached through the co-processor. After a beat was analyzed, a message was sent to the co-processor to display it on the vector scope (from its internal buffer which it uses to pass the data for that individual beat back to the main processor, e.g., the co-processor's output buffer). In another preferred embodiment, the data is copied from the co-processor to the main processor, and is then displayed on the raster monitor through the VGA display card. A high performance display card or a custom raster graphics card may be used to pass the data from the co-processor to the raster display processor directly. In FIG. 1 and FIG. 2, the system 100 with the Vector scope display 116 is shown.

As illustrated, the system 100 uses two separate displays to give maximum flexibility and speed. The system editing, reporting, menus, parameter controls and main user interface functions are optionally implemented using a multi-sync color graphics display 115 driven by a video graphics adapter (VGA) compatible card 113 controlled by coprocessor 112. This gives a pleasant high resolution color graphics display that is not strain producing to the analyst. The superimposition, and most commonly used display sequences have been implemented on the Vector display 116. The Vector display 116 is driven by the Vector driver 117, which gets its data directly from the coprocessor board 112. Alternatively, vector display 116 may be replaced by a raster display controlled by either coprocessor 112 or processor 104.

The system 100 has been designed to be device independent where possible, and this includes the printer device. The system 100 currently implements printing on compatible graphics printers, or a laser printer 118. The printing speed on the laser printer 118 may be enhanced by a Laser Master board 119 that transmits an image to the laser printer 118 instead of character data.

The software that implements the system is divided into Four main logical components: Analog Data Conversion and Collection and Data Analysis Phase, Data Summarization Phase, Patient Data Entry and Analysis Editing, and Report Printing and Digital Data Transmission. These components are loaded by a small integrator program. These different logical modules of the system have been implemented using two different "C" language compilers, assembly language, and the FORTH language on an on-board co-processor. The operating system is Microsoft MS-DOS. Most operating system specific applications have been coded in Microsoft "C", with C-Worthy Screen management libraries from Solution Systems for menu screens. Most scanning analysis related applications have been coded in High-C, a protected mode 32-bit "C" compiler from Metaware Inc. Appendix A describes each of the programs used for system implementation.

Analog data conversion is driven by a Microsoft "C" sub program that is started by the Data analysis Phase program, and runs concurrently with the analysis. The program has routines that start and stop the tape drives of tape reader 122, start and stop the data conversions via A/D converter 124 and log ROM 126, and start and stop the DMA controller board 114. The main data collection loop implements a multi-buffering scheme to ensure that no data overflow occurs during data conversion and collection. The routine that checks the buffers is called at controlled intervals as a background task of the C-Worthy interface library when the system operates in real mode, and a background routine of the Data Analysis Phase program when the system operates in protected mode. The background check routine shares access to the hard disk 110, where digitized data is saved until the next tape is digitized, with the display fetch data routines. These shared access I/O transactions are carefully synchronized.

The Data Analysis Phase is implemented in High-C from Metaware Inc., which executes in Intel 80386 protected mode. The runtime unit is a protected mode runtime such as sold by PharLap Software, Inc. The High-C code is spawned as a shell program from the real mode program. It sets up an interrupt dispatcher to allow communication between the High-C program and the real mode program where DOS services are performed for the High-C program. The High-C Data Analysis Phase program implements the following features in a large processing loop:

- Maintains an interface with the coprocessor board 112 to keep its pipeline fed with digitized data, where the coprocessor board performs the R-peak finding.
- Maintains an interface with the coprocessor board 112 to keep it displaying the digitized data on the Vector display 116.
- Calls routines to perform template matching to classify the current beat.
- Calls routines to classify the current complex. To do this a non-deterministic state machine algorithm has been identified.

For each unrecognized beat, a user interface routine is called to identify it.

Also, a user interface routine is called to allow the analyst to modify analysis parameters, allow the analyst to perform strip labeling and saving, strip measurements, and review of past scanning and statistics. This user interface routine is called at the analyst's request, or when a new complex has been identified.

Also, as scanning progresses, a history file is saved with information about each beat. This file is later used in the Data Summarization Phase to identify Maximum/Minimum heart rates, ST Elevation/Depression maximums, Maximum Pauses Maximum VTACH, Minimum Bradycardia rhythms, etc.

The Data Summarization Phase module of the system is executed after the analysis has been performed, and was designed to off-load some of the processing burden as a batch step. This set of routines was written in "C" language, and is executed by the integrator module as a sequential step after the Analysis Phase. This part of the system calculates maximums and minimums, it places counts in the different system data structures. It ranks different run types, along with pauses, and ST trend analysis. It places all the summarized data into data structures readable by the Analyst Editing functions.

The Patient Data Entry and Analyst Editing Functions set of routines are the second most important interface with the analyst. They allow the analyst to maintain a database of reports, and allow the data entry of patient and diary information. At the end of scanning a tape, the analyst uses the same module to "edit" the collected statistics. The analyst at the end of the analysis may view strips saved during the analysis phase, and may also look at new strips displayable in the color graphics display. The analyst at this point may save the top-ranked heart rate strips, VTACH strips, Brady strips, and ST Elevation and Depression strips.

Using simple menu selections from the displayed menu the analyst may select printing of transmission of reports to remote printers or data receivers. The report printing is implemented using custom high speed algorithms with device drivers for various printers. These are coded in "C" language, and run as a separate module spawned from the integrator module. The data transmission is accomplished by spawning a communications program such as ProComm from DataStorm Technologies with a script file.

FIG. 2 is a block diagram illustrating the data flow of the system 100 according to the invention. Data flow from tape 122 to the disk drive 110 is controlled by the 386 processor 104. Timing of the data flow from the disk drive 110 to display 116 is dependent upon coprocessor 112, digitization of the tape occurs at a rate which is essentially independent of the simultaneous analysis of the waveforms as conducted by both processors and the technician. Digitization and analysis are done by multi-tasking software which calls each process as it is needed.

As the tape reader 122 reads the tape, it generates an analog signal representative of the ECG recorded on the tape. This analog signal is converted into a 12-bit digital signal by analog/digital converter 124. The 12-bit analog signal is then converted into an 8-bit logarithmic signal by the ROM 126 which includes a lookup table as illustrated in TABLE 1.

TABLE 1

| 12 Bit to 8 Bit ROM Lookup Table | |
|---|---|
| INPUT RANGE | COMPRESSED DATA |
| −2048 to −2014 | −128 |
| −2013 to −1948 | −127 |
| −1947 to −1884 | −126 |
| −1883 to −1822 | −125 |
| −1821 to −1761 | −124 |
| ... | ... |
| −991 to −958 | −106 |
| ... | ... |
| −416 to −403 | −81 |
| ... | ... |
| −130 to −126 | −50 |
| ... | ... |
| −52 to −50 | −30 |
| ... | ... |
| −29 to −28 | −20 |
| ... | ... |
| −15 to −14 | −12 |
| −13 | −11 |
| −12 | −10 |
| −11 to −10 | −9 |
| −9 | −8 |
| −8 | −7 |
| −7 | −6 |
| −6 to −5 | −5 |
| −4 | −4 |
| −3 | −3 |
| −2 | −2 |
| −1 | −1 |
| 0 | 0 |

TABLE 1-continued

| 12 Bit to 8 Bit ROM Lookup Table | |
|---|---|
| INPUT RANGE | COMPRESSED DATA |
| 1 | 1 |
| 2 | 2 |
| 3 | 3 |
| 4 | 4 |
| 5 to 6 | 5 |
| 7 | 6 |
| ... | ... |
| 28 to 29 | 20 |
| ... | ... |
| 50 to 52 | 30 |
| ... | ... |
| 126 to 130 | 50 |
| ... | ... |
| 403 to 416 | 81 |
| ... | ... |
| 1884 to 1947 | 126 |

Compression Formula
In = INPUT
CD = COMPRESSED DATA $$CD = ROUND \frac{\{\ln[(|I_n|/30.265153) + 1]\}}{\{0.03304136\}} sgn(In)$$

where $sgn(In) = \begin{cases} 1 \text{ if } In \geq 0 \\ -1 \text{ if } I_n \leq 0 \end{cases}$ This 8-bit signal is provided to the DMA board for copying to RAM 106 and then to disk storage in disk drive 110.

The data is handled in two channels and converted from 12 bits to 8 bits using the Log lookup ROM 126. These two 8 bit values are then assembled as a single 16 bit value which is transferred to the PC using a 16 bit DMA card (off the shelf). Alternatively, the system may use an off the shelf 12 bit a/d converter. This card used 8 bit DMA in the PC. The 12 bit value was positioned in 2 bytes (16 bits) for DMA transfer as two 8 bit bytes.

The tapes are played back at 187.97 times real time, with a sample rate of 133 samples/sec with reference to the patient. This gives a sample rate at the a/d converter of 25,000 sample/sec/channel. Alternatively, the system may play back at 240 times real time, at a sample rate of 133 s/see with reference to the patient, for a sample rate of 31,920 sample/sec/channel. Note there are 2 channels, thus doubling the actual sample transfer rate.

With the a/d cards with 8 bit DMA, this amounted to 2 channels * 2 bytes/sample/channel * 25 Khz = 100 Khz DMA byte transfer rate, or 128 Khz for a 32 Khz sample rate. This is beyond the capabilities of the AT type computers, which have a limited DMA speed capacity. (The older IBM XT could just pass 100 K bytes/sac under some circumstances, so the newer AT compatibles and 386 machines were ironically slower at DMA). However, even 60 Khz was unreliable on the 386 type computers when certain types of screen memory and other accesses to slow peripherals was taking place.

By performing the Log lookup and assembling into 16 bit words for the 16 bit DMA card, a DMA transaction rate of 25 Khz or 32 Khz is achieved. This provides complete reliability, even with screen updates aria other disk transfers occurring simultaneously.

Independent of this storage operation into the disk drive 110, the technician and system are simultaneously evaluating waveforms which are presented on display 116. Coprocessor 112 includes input buffers 112A in which the data from the disk afire 110 is temporarily stored. Coprocessor 112 expands the compressed data at step 128 by employing a table stored in memory which is essentially the reverse of Table 1. For example, the compressed data may be expanded according to Table 2.

TABLE 2

8 Bit to 12 Bit Lookup Table

| COMPRESSED DATA | EXPANDED DATA |
|---|---|
| −128 | −2048 |
| −127 | −1980 |
| −126 | −1915 |
| −125 | −1852 |
| −124 | −1791 |
| ... | ... |
| −101 | −821 |
| ... | ... |
| −80 | −395 |
| ... | ... |
| −20 | −28 |
| ... | ... |
| −10 | −12 |
| −9 | −10 |
| ... | ... |
| 0 | 0 |
| 1 | 1 |
| 2 | 2 |
| ... | ... |
| 5 | 5 |
| 6 | 7 |
| ... | ... |
| 127 | 1980 |

Expansion Formula

CD = COMPRESSED DATA
EXP = EXPANDED DATA
EXP = (30.265153)sgn (CD) ROUND $[e^{|CD|0.03304136} - 1]$
where sgn (CD) = 1 if CD ≧ 0
$\quad\quad\quad\quad\quad\quad$ −1 if CD < 0

After R—peak detection at step 130, the coprocessor moves the data through output buffers 132 for further processing. Initially, the coprocessor is finding R peaks at step 130. At appropriate points, the main processor sends a message to the coprocessor to start processing R peaks. When the coprocessor needs more raw data, it signals the processor to send a disk block of data. At some point, the processor stops the coprocessor so the next beat can be processed for template matching at step 134. The results would now be displayed on the vector monitor. Processor 104 or coprocessor 112 then compares this data to templates which are being created by the technician and stored in RAM 106 by step 134, which could also be processed by the coprocessor. In addition, the software is providing state recognition analysis by step 136, described in detail below, which can be accomplished by either the processor 104 or the coprocessor 112. This information is being displayed and controlled by the technician as indicated on displays 115 and 116.

Referring again to FIG. 1, it can be seen that the system 100 according to the invention is used by a technician for evaluating a Holter ECG tape having a signal representing a series of waveforms thereon and for generating a report reflecting the evaluation. Tape reader 122 constitutes means for generating from the ECG tape an analog signal representative of the ECG waveforms recorded on the tape. Analog/digital converter 124 constitutes means for converting the analog signal into a digital signal. Computer 102 constitutes computing means, including a data bus, a random access memory 106, and a processor 104 for controlling the operation of the system 100 and further including a coprocessor 112. Display 116 constitutes means for displaying the waveforms representing ECG. Controller 108 and disk drive 110 constitute a storage device connected to the data bus. DMA board 114 constitutes a direct memory access means connected between the data bus and the A/D converter 124 for storing the digital signal via the RAM 106 to the disk drive 110 while processor 104 and coprocessor 112 are used by the multitasking software to simultaneously analyze data from the disk drive 110. Preferably, computer 102 has an industry standard architecture substantially compatible to the IBM AT bus structure. Processor 104 generates a file including information for the report based on instructions from the technician provided by keyboard 128.

Preferably, converter 124 is a 12-bit converter and provides the 12-bit digital signal to ROM 126 which includes a LOG look-up table. The LOG look-up table converts the 12-bit digital signal into an 8-bit digital signal so that the resolution of the low magnitude digital signals are substantially preserved while the higher magnitude digital signals are represented with fewer bits. FIG. 4 is an example of one preferred embodiment of such a look-up table. A multiplexer 400, which may be part of the A/D converter 126, switches between the two channels from the tape reader 122. When the sample from one channel is converted by ROM 126, its 8 bit log lookup value is stored in a latch 402. When the sample from the other channel is converted, its 8 bit log lookup value is presented via lines 404 in parallel with the data stored in the latch 402 to the 16 bit DMA card 114.

The system 100 employs a template matching technique at step 134 to determine if a beat is normal (N) or ventricular ectopy (VE) or some other classification. Waveforms identified by the technician as templates for normal beats are matched to waveforms being scanned or being evaluated by processor 104. When converted to digital form, each waveform is essentially a series of digital values representing the magnitude of the waveform at various intervals. Matching is accomplished by determining the difference between the value at various points of the waveform being measured and the value at corresponding points of each template. A match is defined as any sum of the absolute value of each of the differences within a preset range. The sequential order is determined by placing at the beginning of a queue the last hemplate which has been matched and wherein the waveform being evaluated is compared to templates in the queue starting with the template at the beginning of the queue and proceeding through the queue. The closest match is called the matching template. If no template matches, the operator must classify.

Template difference calculations employ the following formulas:

$$A = \frac{1}{N} \sum_{i=1}^{N} S_i \quad\quad (1)$$

$$C_i = S_i - A \quad\quad (2)$$

$$D_k = \sum_{i=1}^{N} |T_{k,i} - C_i| \quad\quad (3)$$

$$D_{k,j} = \sum_{i=1}^{N} |T_{k,i} - T_{j,i}| \quad\quad (4)$$

A match is only allowed if $$D_k < P \rightarrow \text{MATCH} \quad\quad (5)$$

where P is a preset value which may be a preset function of the size of the current beat or of the sequence C; and where $S_i$ = time series of N raw samples comprising a 200 msec segment around the R-peak
A = average of N samples and represents the base line
$C_i$ = corrected sequence with average baseline removed
$T_{k,i}$ = time series of corrected samples from $C_i$ of saved beats for each template K
$D_k$ = distance of current beat to template K
$D_{k,j}$ = distance of template k to template j
$M_k$ = minimum of $D_{k,j}$ for all all j, where j is s different category than k If more than one match is found, the closest match is used, e.g., the one with the smallest $D_k$. In one preferred embodiment, N=13 samples may be used.

Furthermore, in order to minimize the search operation and quickly find a match, the processor maintains a value called a minimum template difference $M_k$ for each template which corresponds to the minimum of the sums of the absolute value of the differences between the value at various points of the template and the value at corresponding points of another template of a different classification. The comparison is discontinued when a match is found by equation (5) (or by the mathematical equivalent form of equation (5)) and the minimum template difference $M_k$ between the matched template and every other template of a different classification is more than twice the difference $D_k$ between the waveform being evaluated and the matched template k. For example, suppose that all waveforms are either ventricular ectopy (VE) or normal (N) and a waveform being evaluated falls within a preset range of a normal template and has a difference value of 8. Also suppose that this matched template has been compared to all other VE templates and the comparison yielded a minimum template difference value of at least 16 between the matched template and every other VE template. By the triangle inequality law, it would not be possible by searching through the VE templates to find a template which is closer than the matched template so that the search can be discontinued, declaring the beat to be normal (N).

In addition, the system includes software for analyzing the series of waveforms according to a nondeterministic logic state analysis as illustrated in FIG. 6. This analysis permits the system to indicate when the series of waveforms correspond to ventricular ectopy (VE), bigeminy, VE pair, and ventricular tachicardia.

As shown in FIG. 3A, a standard waveform has a P wave, a QRS complex and a T wave. As is well known in the prior art, the QRS complex (herein the R wave) is generally identified by its major peak. The T wave is then identified as the first peak after the R wave. FIG. 3B is an example of an R wave template. In addition, the system 100 according to the invention employs a T wave template as illustrated in FIG. 3C. The T wave template permits processing of the wave more quickly and inadvertent recognition of a T wave as an R wave is minimized.

The method for T wave rejection is as follows. When an R-peak is identified, and the template is found to be VE or Non-VE, then a specified elapsed time is allowed before another R-peak may be recognized. This time is set by the operator, usually 200-350 ms. A separate time is specified after VE's than after other beat types, since some VE's have an especially nasty tail which is hard to avoid. This is a common industry practice.

If the system triggers on a T wave, thinking (erroneously) that it is an R-peak, then the operator must skip it, rejecting it or calling it artifact. The system will stop on the T wave if the other rules for avoiding it fail because the system cannot rule out the possibility that it is simply an R-peak whose shape does not have a template. The operator is asked to classify it, just as for any R-peak which does not match a template.

The T wave template is a classification that the operator may apply when asked to classify the 'beat'. In the future any peak which matches T wave templates is totally ignored, as though no peak had been found at the position. The recognition of the T wave template does not have any temporal or sequential significance to other beats or beat peaks in the present implementation, just if a 'beat' or peak matches a T wave template, it is ignored. The temporal significance of the T wave is that real T waves occur right after the R peak.

The system may not function with high accuracy if the operator incorrectly classifies a T peak that is or looks like a real beat, because that type of beat will be ignored. Therefore, the method is used as a last resort, when setting the other parameters does not help, which can occur with patients who have especially peaked T waves.

Referring to FIGS. 5 and 6, nondeterministic state evaluation according to the invention will be described. Nondeterministic state evaluation differs from deterministic or normal state evaluation because more than one state can be present at the same time, and the next state can actually be more than one state (branching) or the next state can be no state at all (termination). The proper execution of a nondeterministic state system requires a data structure for each simultaneously active state. FIG. 5 shows a flow chart of the evaluation process which is carried out by software which instructs the processor, although the coprocessor may be used. The purpose of the evaluation is identify recognized state such as a VE pair, V tachicardia or bigeminy. Once a recognized state is achieved, the evaluation is terminated. Each recognized state is enclosed in a double line. Each beat could begin a series which results in one or more of the states to be recognized. Therefore, the evaluation process of FIG. 5 is applied to each beat. In the FIG. 5 flow chart, letters A-L represent various states. The arrows indicate the beat classification needed to progress to the next state. For example, from START, state A is present if a normal beat N occurs and a ventricular ectopy state VE is present if a ventricular beat V occurs. To proceed from state A to state B, a ventricular beat v must be the next occurring beat. If the next beat after state A is normal, the evaluation is terminated as indicated by END. States marked with an asterisk * add to the count of the recognized beats of that sequence, if the sequence terminates in a recognized state.

The evalation process of FIG. 5 will now be described by applying it to the beat sequence illustrated in FIG. 6. In nondeterministic state evaluation according to the invention, beats 1-20, labeled as an example, would each be evaluated, one at a time. Sequences S1-S20 correspond to the evaluation of beats 1-20, respectively. Beat 1 is a normal beat N which begins a new sequence S1 which advances from START to state A. Beat 2 is a normal beat N which terminates sequence S1 and which begins a new sequence S2 which advances from START to state A.

Beats 3–9 constitute bigeminy and are recognized as follows. Beat 3 is a ventricular beat V which advances sequence S2 to state B and which advances sequence S3 to recognized state VE, terminating sequence S3. Beat 4 is a normal beat N which advances sequence S2 to state C and which begins a new Sequence S4 which advances from START to state A. Beat 5 is a ventricular beat V which advances sequence S2 to state F, which advances sequence S4 to state B and which begins a new sequence S5 which advances from START to recognized state VE, terminating sequence S5. Beat 6 is a normal beat N which advances sequence S2 to state G, which advances sequence S4 to state C and which begins a new sequence S6 which advances from START to state A. Beat 7 is a ventricular beat V which advances sequence S2 to state H to set the bigeminy flag BF, which advances sequence S4 to state F, which advances sequence S6 to state B and which begins a new sequence S7 which advances from START to recognized state VE, terminating sequence S7. Beat 8 is a normal beat N which advances sequence S2 to state I, which advances sequence S4 to state G, which advances sequence S6 to state C, which begins a new sequence S8 which advances from START to state A. Note that a ventricular beat will cause state I to progress to state J and K simultaneously, as indicated by dual path 500. Beat 9 is a ventricular beat V which advances sequence S2 to state J, which begins a new sequence S2' which advances from state I of sequence S2 to state K, which terminates sequence S4 because the bigeminy flag BF was set by beat 7, which advances sequence S6 to state F, which advances sequence S8 to state B and which begins a new sequence S9 which advances from START to recognized state VE, terminating sequence S9.

Beat 10 is a normal beat which loops sequence S2 back to state I, which terminates sequence S2', which advances sequence S6 to state G, which advances sequence S8 to state C and which begins a new sequence S10 which advances from START to state A.

Beats 11 and 12 constitute a VE pair and are recognized as follows. Beat 11 is a ventricular beat V which advances sequence S2 to state J, which begins a new sequence S2" which advances from state I of sequence S2 to state K, which terminates sequence S6 because the bigeminy flag BF was set by beat 7, which advances sequence S8 to state F, which advances sequence S10 to state B and which begins a new sequence S11 which advances from START to recognized state VE, terminating sequence S11. Beat 12 is a ventricular beat V which terminates sequence S2, which advances sequence S2" to the recognized BIGEMINY state terminating sequence S2" and clearing the bigeminy flag BF, which terminates sequence S8, which advances sequence S10 to state D and which begins a new sequence S12 which advances from START to recognized state VE, terminating sequence S12.

Beat 13 is a normal beat N which advances sequence S10 to the recognized state VE PAIR terminating sequence S10, and which begins a new sequence S13 which advances from START to state A.

Beats 14–16 constitute a run of ventricular tachicardia and are recognized as follows. Beat 14 is a ventricular beat V which advances sequence S13 to state B and which begins a new sequence S14 which advances from START to recognized state VE, terminating sequence S14. Beat 15 is a ventricular begins V which advances sequence S13 to state D and which begins a new sequence S15 which advances from START to recognized state VE, terminating sequence S15. Beat 16 is a ventricular beat V which advances sequence S13 to state E and which begins a new sequence S16 which advances from START to recognized state VE, terminating sequence S16.

Beat 17 is a normal beat N which advances sequence S13 to recognized state VE TACH terminating sequence S13, and which begins a new sequence S17 which advances from START to state A.

Beat 18 is a single ventricular ectopy VE and is recognized as follows. Beak 18 is a ventricular beat V which advances sequence S17 to state B and which begins a new sequence S18 which advances from START to recognized state VE, terminating sequence S18.

Beat 19 is a normal beat N which advances sequence S17 to state C and which begins a new sequence S19 which advances from START to state A. Beat 20 is a normal beat N which terminates sequence S17 and terminates sequence S19.

As another feature of the invention, a full disclosure file representing the entire series of waveforms on the tape is generated. The file comprises compressed data of limited resolution and limited sampling rates.

The original data is reduced in resolution by skipping, averaging, or otherwise "decimating" samples, only using samples at a rate near 33 samples per second with reference to the patient data. (This is an equivalent rake of 33 samples/sec. of the data generated when the patient was originally monitored by the analog Holter monitor. Of course, the data reading rate off the tape is much faster.) In this system 100, this is accomplished by averaging 4 samples, or by picking one out of every fourth sample. The data is scaled in amplitude (and limited) so that the total excursion is 32 levels. The 32 levels are sufficient resolution to plot on a laser plotter at 200 dots/inch, producing a 0.15" tall waveform. The sample frequency (referenced to patient) is sufficient to see all R-peaks of normal beats by position, and to display the waveforms of ventricular beats sufficiently clearly to be identified.

Figure 7:
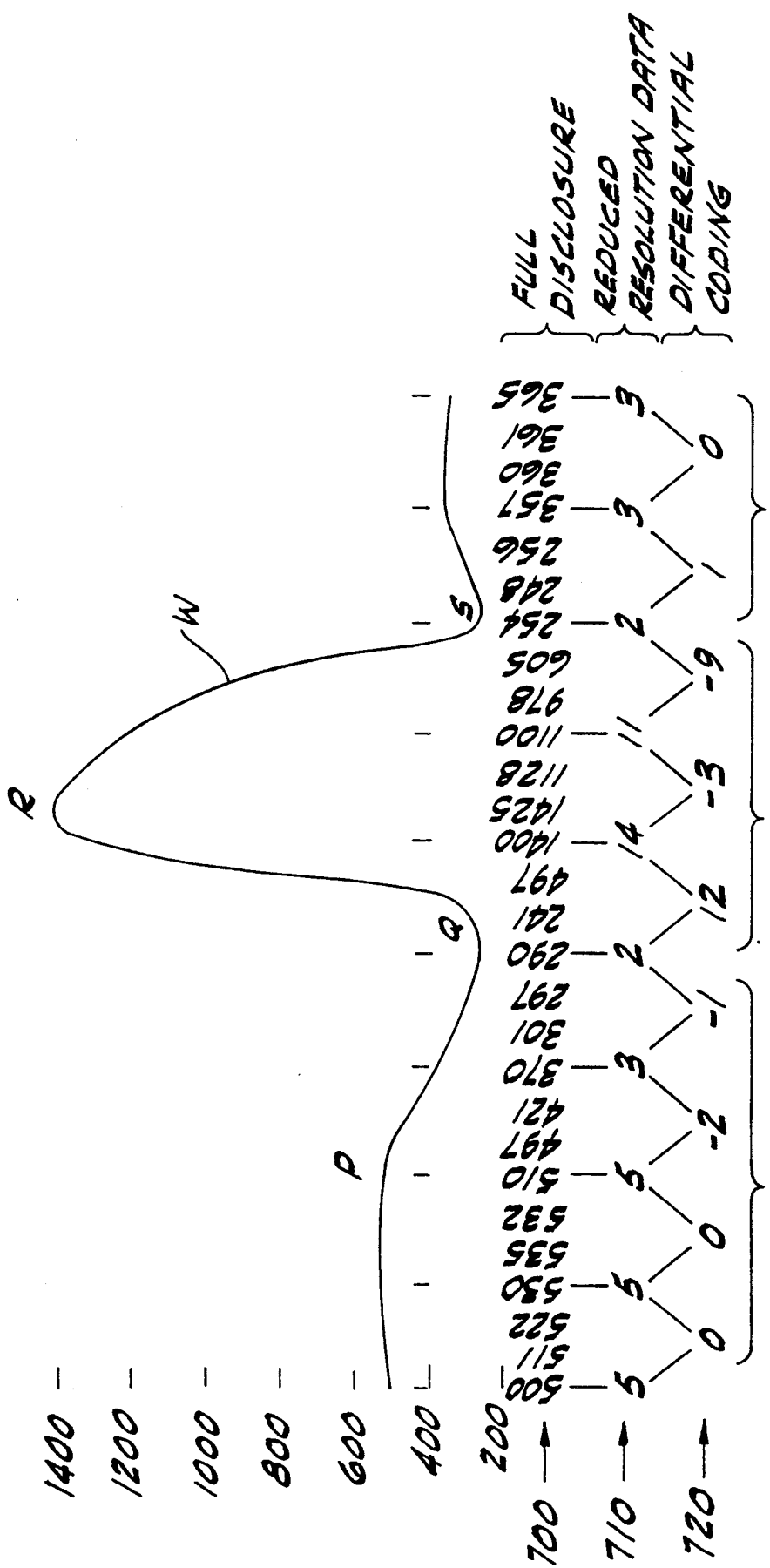
FIG. 7 is an example of the steps involved when generating a full disclosure data file from a waveform and when generating a compressed full disclosure data file using differential coding from the generated full disclosure file.

The data is then further compressed by using a series of coding steps. First the data is converted to differential coding. (This is a version of DPCM, 'Differential Pulse Code Modulation' in the telecommunications industry). Each sample has the previous sample subtracted from it (as the example in FIG. 7 shows). This is a simple, and computationally efficient means to produce codes which consist mostly of the smaller integers near 0. In fact, the output will often have runs of 0s, or +1s, 0, and −1s. Less frequently the differences will be larger numbers (6 to 31), mostly near the R peaks. The differential output is limited to the range −31 to +31.

The data is then encoded further using a variation of 'Huffman' coding, or other codes which use few bits for symbols which occur frequently, and more bits for symbols which occur infrequently. (The symbols to be coded are the 63 integers in the range −31 to 31). This may be combined with run length coding, which is the coding of a repeated sequence of the same symbol with a code representing the sequence in fewer bits than repetitions of the code representing the symbol singly.

The result of this coding is to bring the number of bits to represent a data point down to around 2 to 3 bits. This typically allows 24 hours of data to occupy less than 1 megabyte, where a byte is 8 bits. ($\frac{3}{8}$ byte/ sample

* 33 sample/sec * 60 sec/min * 60 min/hr * 24 hr/tape=1.07 Megabyte/tape). This allows the full disclosure to typically be stored on a single IBM PC compatible 1.2 Megabyte diskette, or transferred by telephone in 10–20 minutes using the new 9600 Baud Modems.

Figure 8:
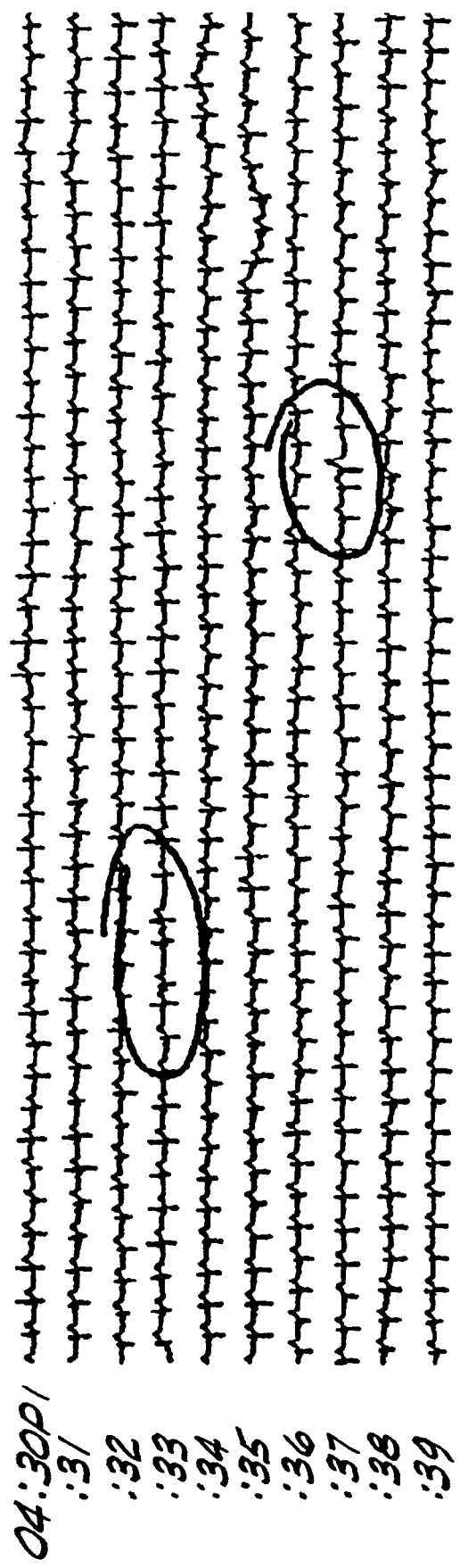
FIG. 8 is an example of a portion of an expanded full disclosure file generated from a compressed full disclosure data file.

For example, FIG. 7 illustrates a waveform W and reference character 700 refers to a series of digitized values representing of the magnitude of the waveform W including a P wave and an R peak. Reference character 710 identifies compressed data corresponding to reduced resolution data. In this example, reduced resolution data 710 has been generated by taking every third sample. Other rates of reduction may be used such as 4, 5, 6, etc., depending on the original sample rate. Reference character 720 refers to differentially coded data which has been generated by subtracting each sample from the previous sample. Taking every third sample provides a limited sampling rate and scaled differential coding provides limited resolution. Further compression, such as run length and Huffman coding, may then be used so that the full disclosure file can be even further significantly reduced in size. The differential values 0, +1, −1, +2, −2 may be seen to occur more frequently than the larger values of 6 to 31 and −6 to −31. If the smaller integer values are represented by codes using two or three bits, then the size of the file can be further reduced. FIG. 8 is an example of a part of a limited resolution, full disclosure file recreated from differentially encoded, compressed data. The circled areas indicate ventricular ectopy and supra-ventricular ectopy which is clearly recognized even though this portion of the file was created from compressed data.

Furthermore, the system includes a function in which the technician can declare any series of waveforms as artifact. However, even though such waveforms are identified as artifact by the technician, template matching is still performed and waveforms which match templates within labeled artifact are still noted and saved.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

APPENDIX A

PROGRAM NAME: ARRMAIN.EXE
MODULE NAME: ADCSUB1.C
MAKE FILE NAME: ARRMAIN.MAK
LINK RESPONSE FILE: ARRMAIN.LNK
MODULES IN THIS PROGRAM: ADCSUB1 ARRMAIN ATHMLIST BTIMEASC CEDARMSG CLIST CW_ADDEN CWBTIME DOSGRAPH FORMSHRT INTERFAC VIEWSTSH
DESCRIPTION

The ADCSUB1.C module contains subroutines for analog to digital data conversion and collection, it contains service routines that supply digital data to the FOX forth board. This set of routines have changed more than any other set of routines in the history of the project. The first time it was written, it was written for a DAS-16 board, later modified for a DAS-20, and finally modified for a PDMA-32 and custom board designed by Elliott Engineering. The PDMA-32 is a board that is designed only for performing DMA data transfers from a proprietary board to the PC's RAM. It's programming is very similar to that of the DAS-16 and DAS-20. Data collection on the PC side of things is done using a set of buffers divided from a single memory allocation. This memory allocation falls on a memory page boundary and is performed by the routine GetBoundaryMemory(). GetBoundaryMemory() is called first thin in ARRMAIN.C to make sure we have enough memory before we proceed with the C-Worthy forms allocations. ADCInit() is called from module ARRMAIN.C. This routine actually controls either a Reel-to-reel device or a Cassette. It starts the capstan of the cassette, then starts to play it. It sets up the DMA controller and begins the data collection process. The saving of the data is done by Monitor_Buff_And_Save() that is called from DOSGRAPH.C. The routine in DOSGRAPH.C is called as a C-Worthy background task, and from DOSGRAPH calls by ARRPROC.EXP. This routine needs to be called from any place where a possible delay may occur that may be longer than the amount that it takes to fill up the buffers (approximately 0.25 seconds). Arrmain may be run in test mode to verify that this limit is not reached. To do this execute from the dos prompt ARRMAIN as follows:

C:/CEDARS>ARRMAIN C -t <RETURN>

Then you will be prompted from arrmain to enter a number from 0–9 for the corresponding dosgraph routine. Use "7" to start the data collection and the timer. Every time a dosgraph routine is entered the clock is restarted, and the time elapsed is displayed when the routine is exited. The routine CheckFilePtrAndWrite() routine is also very important, and care should be taken if it is modified. It causes a side effect to the dos file pointer of the "data.bin" file. This file is being read concurrently by GetDisplayData(). GetDisplayData() is called as a result of a request from the FOX Forth board, through ARRPROC.EXP, down to DOSGRAPH. This routine also moves the file pointer.

The ADCStop() routine stops the appropriate device, shuts off the PDMA-32 board, it frees the ADCbuffer, and sets a flag that the data collection is complete.

The Begin_AtoD_w_DMA() routine is the code that is responsible for setting up the DMA chip, and the PDMA-32 board to perform the conversions, and data transfer. The steps in setting up the chips are critical, and the sequence of events must not be changed. The steps performed by the PDMA-32 and the DMA chip are interleaved. For more information on the DMA 8237 chip and the PDMA-32 board, refer to the METRABYTE PDMA-32 manual, the registers that are written to and read from are completely documented there.

The Shut_Off_PDMA_32() routine disables the DMA chip and the PDMA-32 transfers it also stops the counter.

The set_output_bits() routine set the auxiliary PDMA-32 bits. These bits are used to drive the Reel-To-Reel and Cassette devices. AUX bit one is used to gate data out to the device from the PDMA-32 board. AUX bit two is used to select the PDMA-32 channel to use to collect the data.

The other important function of ADCSUB1.C module is the communication between the Intel 386 processor, and the Fox Computer. A banked switched area of memory is used to move information between the 386 and the Fox board. This Area of memory starts at CC00:0000. The routines in ADCSUB1.C are mainly for reading digitized data, and passing it to the Fox board. See the documentation for foxfunc.c and scan.scf to see what functions are performed by the Fox board. This particular interface uses page 7 (seventh 16K byte page) of the Fox board to pass the data. The routine set_fox_page() is used to tell the Fox board that this is the page we wish to map to. The routine old_fox_page() is used to restore the page that was mapped previously as the mapped page. The read_request() routine gets from the banked memory the read request structure which is the command (or request) from the Fox board, and translates it into variables that are understood by the FoxGetData() routine in Real mode C.

The routine FoxGetData() is called via DOSGRAPH by ARRPROC.EXP to perform Input from the digitized file for processing by the Fox board. The steps that are performed by the routine are as follows: First the current banked switched memory page is saved. This is done, because we do not know what the HighC program ARRPROC.EXP is in process of doing, when the Fox board requested the data. Next, read_request() is called to receive the page offset, file offset to read from, and number of bytes to read. This information was placed in the communication memory area (page 7 of the Fox board) by the software in the Fox board. The page variable tells us the Fox board page to request to be placed as the current bank switched page of the Fox board. The offset tells us the offset of where to write to the information read in. The file offset is lseek location of the file from the beginning of the file. Depending on the status of the data collection, we communicate back to the Fox board by calling write_request(). If the data collection is complete, or the data analysis is now caught up with the data collection, a write_request() is made and the routine returns. Otherwise, we make sure that the file pointer has not been moved (by the digitize write routine) and make our read operation. After the read operation we communicate success to the fox board with a call to write_reques().

NOTE: For complete details on what the data structures, and the communication between the Fox board and the Intel 386 processor is performed, please see the SCAN.SCF and foxfunc.c documentation.

PROGRAM NAME: ARRMAIN.EXE
MODULE NAME: ADCSUB1.C
MAKE FILE NAME: ARRMAIN.MAK
LINK RESPONSE FILE: ARRMAIN.LNK
MODULES IN THIS PROGRAM: ADCSUB1 ARRMAIN ATHMLIST BTIMEASC CEDARMSG CLIST CW_ADDEN CWBTIME DOSGRAPH FORMSHRT INTERFAC VIEWSTSH
DESCRIPTION

The ARRMAIN.C module contains the mainline of the "SCANNING" part of the CEDARS' system. This includes digitizing in module ADCSUB1.C, and C-Worthy user interface in module DOSGRAPH.C. The rest of the modules are supporting routines to the DOSGRAPH.C routines. From ARRMAIN.C the HighC runtime is executed to run the protected mode program ARRPROC.EXP which does the "SCANNING". Also, from here the data collection module is called to start the digitizing of the data from the cassette or Reel-to-reel player.

The HighC program ARRPROC.EXP communicates with, and executes real modes subroutines of ARRMAIN.EXE. This is accomplished with a little magic. An interrupt service routine is set up by calling intsetup(), an assembly language routine, before the run386 runtime is started. Then when the protected mode program wants to execute a real mode subroutine, it sets off an interrupt (int 85), and control is passed to the C routine int_dispatch() in the DOSGRPAH.C module. Communication between the HighC ARRPROCE.EXP program and DOSGRAPH.C interrupt routines is done by using the cpu's registers. The registers carry the routine number that the dispatch routine is to execute, and the address of a data structure that communicates parameter values that are modified using C-Worth routines. This communication is better explained in the documentation for INTERFAC.ASM and DOSGRAPH.C.

???????

PROGRAM NAME: CEDARMM.EXE, ARRMAIN.EXE
MODULE NAME: ATHMLIST.C
MAKE FILE NAME: CEDARMM.MAK, ARRMAIN.MAK
LINK RESPONSE FILE: CEDARMM.LNK, ARRMAIN.LNK
DESCRIPTION

This module contains all the routines that are needed to build, select from, and get information from a heart rythm comment list. They are used in the analyst impressions form (module VIEWSTRP.C), and for selection by the user while scanning (module DOSGRAPH.C). The rythm comment list is a simple C-Worthy list created by using AppendToList(). The selection routine is implemented using the C-Worthy List() routine.

PROGRAM NAME: CEDARMM.EXE/ARRMAIN.EXE/PRINTRPT.EXE
MODULE NAME: BTIMEASC.C
MAKE FILE NAME: CEDARMM.MAK/ARRMAIN.MAK/PRINTRPT.EXE
LINK RESPONSE FILE: CEDARMM.LNK/ARRMAIN.LNK/PRINTRPT.LNK
DESCRIPTION

The BTIMEASC.C module contains a routine to convert a long integer to a formatted ASCII string in the form HH:MM:SSXN where HH is hours in 12 hour format, MM is minutes, SS is seconds, X is "P" for PM and "A" is for AM, and N is for the day number 1, 2, or 3. The module also contains a routine to convert from the ASCII form to a long. The BtimeAsc() subroutine allows for several return formats, according to the display flag that it is passed. These format are: BT_MIDDLE which gives an ASCII string in the form of HH:MM:SSXN. BT_LONG which gives HH:MM:SS:TXN where T is tenth's of a second. BT_ELAPSE which gives HH:MM:SS. BT_SHORT_HOUR which returns number of hours in the form of HHH. BT_HOUR gives an ASCII string in the form HHXN.

The following are a listing of all the C language modules. This is a checklist, of all programs that have been documented.

| NAME | EXT | SIZE | MOD DATE | | DOC FLAG | USED BY PROGRAMS |
|---|---|---|---|---|---|---|
| ADCSUB1 | C | 21760 | 7-22-89 | 9:07p | X | ARRMAIN |
| ANALYZE | C | 16896 | 6-12-89 | 12:53p | | ARRPROC |
| ARRMAIN | C | 2069 | 8-23-89 | 10:28P | X | ARRMAIN |
| ARRPROC | C | 79012 | 8-27-89 | 2:43a | | ARRPROC |
| ARRSUPS | C | 5284 | 2-26-89 | 4:46p | | ARRPROC |
| ATHMLIST | C | 10240 | 4-07-89 | 1:00P | X | CEDARMM/ARRMAIN |
| BEATMGT | C | 8320 | 4-24-89 | 9:50a | | ARRPROC |
| BRESSTAT | C | 1152 | 10-31-88 | 11:29a | | PRINTRPT |
| BTIMEASC | C | 5776 | 10-20-88 | 10:53a | X | CEDARMM/ARRMAIN/PRINTRPT |
| BUGPLOT | C | 1071 | 12-06-88 | 3:15p | | |
| CEDARFLD | C | 61044 | 8-27-89 | 3:16a | X | CEDARMM |
| CEDARMM | C | 13678 | 8-26-89 | 9:57p | X | CEDARMM |
| CEDARS | C | 1796 | 10-20-88 | 10:40a | ? | no longer used |
| CLIST | C | 1920 | 7-05-89 | 9:29p | X | CEDARMM/ARRMAIN/ARRPROC |
| COUNTSCR | C | 14592 | 6-09-89 | 5:25p | | ARRMAIN |
| CWBTIME | C | 6740 | 11-20-88 | 4:08p | X | CEDARMM/ARRMAIN |
| CW_ADDEN | C | 5445 | 8-24-89 | 12:14a | x | CEDARMM/ARRMAIN |
| DAS20FUN | C | 1910 | 12-06-88 | 4:53p | | no longer used |
| DISPSCOP | C | 11008 | 2-24-89 | 3:26p | | ARRPROC |
| DOSGRAPH | C | 30101 | 8-26-89 | 5:57& | X | ARRMAIN |
| DOTLINE | C | 3200 | 10-31-88 | 12:28p | | PRINTRPT |
| EDITS | C | 89075 | 8-26-89 | 9:30a | X | CEDARMM |
| FILECOPY | C | 1952 | 10-20-88 | 10:41a | | |
| FILETST | C | 10368 | 4-23-89 | 4:56p | | |
| FORM | C | 21346 | 11-06-88 | 11:20p | | CEDARMM/ARRMAIN |
| FORMPROC | C | 4750 | 1-20-89 | 8:58p | | CEDARMM |
| FORMSHRT | C | 3401 | 2-20-89 | 7:53p | | ARRMAIN |
| FOXFUNC | C | 21481 | 8-21-89 | 8:20p | | ARRPROC |
| FOXTERM | C | 512 | 12-16-88 | 7:48p | | ARRPROC |
| FOXTEST | C | 1536 | 12-18-88 | 1:26p | | |
| FREEFRM | C | 4453 | 10-20-88 | 10:42a | X | CEDARMM |
| FUNCSBIN | C | 18198 | 8-26-89 | 6:46p | X | CEDARMM/ARRMAIN/PRINTRPT |
| GETDATA | C | 6939 | 8-21-89 | 8:19p | | ARRPROC |
| GETDEV | C | 2972 | 10-14-89 | 7:00p | X | ARRPROC/CEDARMM |
| GREPSON | C | 13696 | 11-01-88 | 10:15a | X | PRINTRPT |
| GRSTORE | C | 6656 | 11-10-89 | 1:54a | X | PRINTRPT |
| HERSH | C | 3840 | 3-17-89 | 10:58a | | PRINTRPT |
| IGRAPH | C | 19968 | 10-31-88 | 7:59p | | PRINTRPT |
| INTERFAC | ASM | 2432 | 5-05-88 | 5:11p | X | ARRMAIN |
| JOYSTICK | C | 3456 | 5-06-89 | 3:12p | | ARRPROC |
| LASER | C | 91 | 10-20-88 | 10:42a | | PRINTRPT |
| LASER_M | C | 9088 | 11-10-88 | 9:20a | | PRINTRPT |
| OUTTEXT | C | 774 | 12-06-88 | 8:15p | | PRINTRPT |
| PATSCR | C | 21228 | 8-27-89 | 12:43a | X | CEDARMM |
| PICKEST | C | 6614 | 1-02-89 | 12:04a | X | CEDARMM |
| PRINTOPT | C | 97135 | 8-27-89 | 2:43a | X | PRINTRPT |
| PRINTRPT | C | 5504 | 4-23-89 | 4:57p | X | PRINTRPT |
| RAMMGT | C | 12032 | 2-07-89 | 4:15p | | ARRPROC |
| RECOGNIZ | C | 21248 | 7-05-89 | 9:33p | | ARRPROC |
| REPORT | C | 6133 | 8-26-89 | 9:33p | X | CEDARMM |
| RGROUP | C | 34572 | 10-29-88 | 12:31p | X | CEDARMM |
| RGROUP2 | C | 3259 | 8-21-89 | 11:19p | | no longer used |
| RPTFORM | C | 5718 | 8-26-89 | 9:51p | X | CEDARMM |
| RUN | C | 1407 | 2-25-89 | 2:32a | X | RUN |
| R_PEAK | C | 8608 | 12-06-88 | 8:05p | ? | used as algorithm for Fox |
| SCAN | SCF | 47360 | 6-12-89 | 3:03p | | FOX BOARD FORTH SOURCE |
| STRPINFO | C | 739 | 10-29-88 | 3:14p | X | CEDARMM/ARRMAIN/PRINTRPT |
| SYSCPY | C | 608 | 10-20-88 | 10:50a | ? | no longer used |
| TABLES | C | 31573 | 8-27-89 | 4:13a | | TOTABLE |
| TESTICK | C | 2239 | 10-20-88 | 10:54a | ? | joystick calibration |
| TEXTINFO | C | 1544 | 3-20-89 | 10:45a | | ARRPROC |
| TOTABLE | C | 1664 | 4-23-89 | 4:57p | | TOTABLE |
| TRIANGLE | C | 2560 | 2-08-89 | 6:01p | ? | test routine |
| VIEWSTRP | C | 31603 | 8-27-89 | 3:45a | X | CEDARMM |
| VIEWSTSM | C | 2425 | 1-26-89 | 6:09p | X | ARRMAIN |

PROGRAM NAME: CEDARMM.EX
MODULE NAME: CEDARFLD.C
MAKE FILE NAME: CEDARMM.MAK
LINK RESPONSE FILE: CEDARMM.LNK

DESCRIPTION
The module CEDARFLD.C contains all the subroutines that are called as Action procedures, or Validate procedures from C-Worthy forms. An Action proce-

| MODULES IN THIS PROGRAM: | | | | |
|---|---|---|---|---|
| ATHMLIST.C | BTIMEASC.C | CLIST.C | CEDARFLD.C | CEDARMM.C |
| CEDARMSG.MLC | CW_ADDEN.C | CWBTIME.C | EDITS.C | FORM.C |
| FORMPROC.C | FREEFRM.C | FUNCSBIN.C | PATSCR.C | PICKLST.C |
| REPORT.C | RGROUP.C | RPTFORM.C | STRPINFO.C | VIEWSTRIP.C | dure is called before the user is allowed to edit the field that is being highlighted. A validate procedure is called after a user presses a valid exit key when the field is being edited. Action procedures and Validate procedures have been used in many ways, including moving data from the field to the global data structures, display of related data such as in the Analyst impressions form, when a time field is edited, the Validate procedure allows display of graphics data at the point in time.

Also contained in the CEDARFLD.C module is the SetFile() subroutine that reads the data structures associated with a patent (log number). It reads only the files that have been created up to this point according to the processing flags found in the patHdr structure.

The first few subroutines in CEDARFLD.C from SetFile() upto GenUpdate() relate to the patient data entry form, and diary entry form. These mainly copy the data field to the data structure.

The GenUpdate() subroutine is responsible for moving the repeated data group data that is displayed by the genForm() routine found in EDITS.C module. This routine moves the fields of each repeated data group to the corresponding data fields in the data structures, such as genHdr, brdHdr, pcmHdr, and sveHdr.

The DryUpdate() subroutine moves the repeated data group data that is displayed by the dryEdit() routine found in EDITS.C module. This routine moves the data fields of the form into the dryHdr global data structure.

The Strip RGroupInit() subroutine updates the currentElement, currentField, and topElement of the repeated data group of strips in the analyst impressions form. This is the Validate routine for the time field in the repeated data group to display the strips. When the time field is highlighted, the corresponding strip is displayed in VGA/EGA graphics. On the return from the viewstrip() subroutine, if the user has moved through some of the strips in graphics mode, the repeated group display needs to be updated. This is done by using two global variables updated in viewstrip.c, and then used here to set the current repeated group field.

The routine CreateStripGroup() is the routine that displays, and allows moving through graphics displayed strips. It formats and passes the top line of the graphics display to viewstrip(). The routine MoveInsideRepeatedGroup() that is used in this subroutine became a static subroutine when we went from C-Worthy v.98b to v1.0. That is why we have our own version of RGROUP.C that is compiled/linked instead of included from the C-Worthy library.

The routine CreateNewStripValidate() is the validate routine used in all other time fields in the Analyst Impressions form. This routine passes control to ViewNewStrp() to display a strip in VGA/EGA graphics at the specified time. The routine ViewNewStrp() makes sure that the digitized data matches that of current log number. This routine passes the current field number to ViewNewStrp(). This is done so that ViewNewStrip() knows which top ten structure to use to allow a user to change the current highest heart rate, minimum heart rate, max st elevation etc. The routine also updates the C-Worthy fields that were modified if a new top ten element has been chosen.

NOTE: If you are thinking of modifying this routine, I wish you luck!! Most of the C-Worthy system crashes have come from here. I will give you a few words of advice. If you modify the screen layout, make sure you track from strForm(), through here, to ViewNewStrip the field numbers. Also make sure when the data is placed back into the C-Worthy data fields, you cast it to the right value. If you don't, you'll be walking on some other variable's memory.

The routine CreateNewStrip() is there to fool you. It really is not called by an program. It fooled me when I first started adding the ability to display title lines on the strips.

The BrdUpdate() routine is the validate routine for the brady profile repeated data group form. It moves data from the displayed C-Worthy data fields to the corresponding data structures.

The VenUpdate() routine updates the ventricular ectopy profile repeated data group from. It moves data from the displayed C-Worthy data fields to the corresponding data structures.

The VenValidateTotal() routine is called any time a field is updated in the ventricular ectopy profile. This is done to keep the totals updated in the display.

The StrDelete() routine used to delete a strip from the analyst impressions screen, but since the graphics file also needed to be updated, it was decided to just mark the items on the repeated group as deleted. This made this subroutine obsolete.

The MarkStripDel() routine is called as a delete routine from the strip repeated data groups from the analyst impressions form. It marks the strip on which the delete key was pressed as deleted.

The strUpdate() routine is used as the repeated data group validate routine to move the screen data fields to the strHdr global structure.

The PcmUpdate() routine is the validate routine for the pacemaker profile. It is used as the repeated data group validate route to move the screen data fields to the pcmHdr global structure.

The SveUpdate() routine is used to update the repeated data group fields for the supraventricular ectopy table.

The SveValidateTotal() routine is used to keep the totals updated when a field in the repeated data groups of the supraventricular ectopy table is modified.

The CalcFlds() routine moves the screen data fields from the AnalystForm to the genHdr structure, and it also updates the st depression totals. This routine is the validate routine for ST fields in the analyst impressions form.

The routine CaptureName() is the validate routine for the transmit file name in the report form. It copies the file name string from the C-Worthy data area to the tapeHdr global structure.

PROGRAM NAME: CEDARMM.EXE
MODULE NAME: CEDARMM.C
MAKE FILE NAME: CEDARMM.MAK
LINK RESPONSE FILE: CEDARMM.LNK

| MODULES IN THIS PROGRAM: | | | | |
| --- | --- | --- | --- | --- |
| ATHMLIST.C | BTIMEASC.C | CLIST.C | CEDARFLD.C | CEDARMM.C |
| CEDARMSG.MLC | CW_ADDEN.C | CWBTIME.C | EDITS.C | FORM.C |
| FORMPROC.C | FREEFRM.C | FUNCSBIN.C | PATSCR.C | PICKLST.C |

| MODULES IN THIS PROGRAM: | | | | |
|---|---|---|---|---|
| REPORT.C | RGROUP.C | RPTFORM.C | STRPINFO.C | VIEWSTRP.C |

DESCRIPTION

This set of routines implement the main menu of CEDARS system. The menu is implemented using C-Worthy Interface Library menu system. C-Worthy is a very powerful and flexible set of callable routines, and therefore make these routines complicated to use. As is evident in later modules, the techniques for using these routines has improved as the project has progressed.

This program is executed from the RUN.EXE program. Please refer to the RUN documentation to see it's interaction with the rest of the system. CEDARMM is the program that is executed after every step in the analysis process. The first step is data entry. For a new patient, selecting the first menu item will execute PATSCR, which will bring up a form to allow the energy of patient demographics, and other patient information. After patient data energy, the Tape is digitized, and scanned. This is done by selecting the second menu, and either "SCAN CASSETTE" or "SACN REEL-TO-REEL". By selecting one of these options, this program is exited with an exit code greater than 200, and the RUN program interprets this and will execute ARRPROC which executes in real mode. The next step in the analysis process is data reduction, which is accomplished in the program TOTABLES.EXE, and then this data may be viewed and/or edited by using the next set of menu items. And then Analyst reports may be printed with the next set of menu items.

C-Worthy must be initialized, and we have implemented our own version of the initialization routine. This version does not implement the header as is implied in its name; InitUtilityNoHeader. The parameters to this routine are two message names, and the name of the Help context library. The two message names are define's kept in a file called cedarmsg.mln. The test that they stand for is stored in a file called cedarmsg.mlc. These two files are maintained by the message librarian program MSGLIB. All text strings displayable by the system are stored in these two central libraries. These two files should not be modified, except by using MSGLIB.

The system help has not been fully implemented, and is left as a future enhancement for the system. Help can be made available at any level, simply by pushing the current help context, and enabling a new one.

Throughout the system, all the table variables where analysis data are stored are available globally. These variables are cleared in the first part of cedarmm.c, which will be later read in from the patient's data files. Also there are some control flags that control what parts of the program may be executed. These flags tell how far the analysis of this patient has proceeded. The are maintained within CEDARMM only. The main routine can be executed with no parameters, or with a continuation flag. If the program is started with the continuation flag, the SetFile routine is called to fill the tables with the data. Otherwise, only after selecting the first or third options of the first menu will there be patient data available.

The WindowStyleMenu routine displays the menu that is created by a call to SetupMainMenu. SetupMainMenu creates a menu structure in a C-Worthy list. WindowStyleMenu is one of the C-Worthy supplied routines. When a selection is made by the user, the routine will can MainMenuAction. All other routines are called from MainMenuAction.

Since this program calls routines that change the screen considerably from module to module, the screens are saved at the beginning of MainMenuAction. ActivatePalette, AllocateArray, and SaveZone are all C-worthy routines.

The WindowStyleMenu routine passes the menu selection to MainMenuAction. The corresponding routine is executed only if the flag has been set to indicate that it is allowed to execute this part of the program at that stage of the analysis. A routine ChangeMessageLine is used to aid the user by displaying control keys at the bottom of the display. This routine is called accordingly at each menu option. This routine is implemented similarly to the printf statement. The message text has imbedded in it "%s" to display the text that corresponds to the key values supplied as parameters to the routine.

The WindowStyleMenu routine passes a value of "−1" to the MainMenuAction routine if the user pressed the ESCAPE key. If this option is chosen, the C-worthy routine VerifyProgram Exit routine is called.

The first menu option of the first menu category executes the patient data entry screen. The second menu option of the first menu category executes the diary data entry screen. The third option executes a list selection routine, that allows the user to select from all currently available analysis data. It displays a list of all current patient reports. The user may select from these, and the data will be available for display or edit.

From the second category, the user may scan a Cassette tape, a Reel-To-Reel tape, or rescan the current digitized data that is stored on the harddisk. When any of the three menu items are chosen, the routine writes out the current tape number and flags, writes out the edited data, and exits the program with an exit code of 201, 205, or 202. This causes the RUN program to execute ARRPROC a program written in HIGH-C, a real mode implementation of C.

From the fourth menu category, the report editing function may be selected. The fourth menu category is displayed before the third menu category in the window style menu. The first menu choice here is the Analyst impressions screen. Here the top heart rate, lowest heart rate, st highs and lows, top vtach rate, lowest brady rate, longest pauses, strips and other graphics related data can be viewed. From here any part of the tape may be reviewed, including typing in a time, and displaying the exact waveforms that occurred at that time. The analyst may from this screen reject possible erroneous data classified as the highest or lowest one of the classifications. Also, new strips may be saved at this point, and added to the current strip list. The analyst impressions screen is implemented using a C-Worthy form, and this form definition may be found in "edits.c" as strDisp().

The next menu items in this category are the general table, the ventricular ectopy table, and the freedom paragraph entry screens. All these are implemented as a C-Worthy form. There are other tables, that are currently disabled, they are functional, and all that needs to be done is to uncomment them. These have been disabled, because several of the fields of information have duplicate entries in the general table, on the ventricular table. See the documentation in EDITS/DOC for further information on the implementation of the forms.

PROGRAM NAME: CEDARMM.EXE, ARRMAIN.EXE
MODULE NAME: CEDARMM.C
MAKE FILE NAME: CEDARRMM.MAK, ARRMAIN.MAK
LINK RESPONSE FILE: CEDARMM.LNK, ARRMAIN.LNK
DESCRIPTION

The CLIST.C module is used during scanning of a tape by ARRPROC.EXE. This routine declares and initializes the beat_info array, and the beat priority sequence length and interleave arrays.

Priority is used helping the non-deterministic state machine that identifies the beat sequences. The higher the priority, the higher the importance that the path is given over another.

The sequence length is used to help identify limited length (in number of beats) beat sequences, like a VE Pair is of length 2. A length of 0 is used to label sequences that may be unlimited in length, like VTACH.

The interleave is used to identify the interleave of NORMAL beats with ABNORMAL beats, like a bigeminy which has an interleave of 2.

The display count column of the beat_info array identifies those beat sequence types that need to be counted and displayed.

PROGRAM NAME: CEDARMM.EXE, ARRMAIN.EXE
MODULE NAME: CEDARMM.C
MAKE FILE NAME: CEDARRMM.MAK, ARRMAIN.MAK
LINK RESPONSE FILE: CEDARMM.LNK, ARRMAIN.LNK
DESCRIPTION

The CWBTIME.C module defines the subroutines that make up a user defined C-Worthy type. The routines have entries in the structures of formproc.c and formproc.h. The type that is defined in these routines have the following format: HH:MM:SSXN where HH is Hours in 12 hour format, MM is minutes, SS is seconds, X is either a "P" for PM or "A" for AM, and N is for the day number 1, 2 or 3.

A user defined type needs several routines so that it may be used by the C-Worthy calls: An allocate routine, that allocates spaces for the field data type, and points the data field pointer to the space. A destroy procedure that deallocates the space of the data field. A edit procedure, which is called when a cwbtime field is highlighted by a routine like EditForm(). This routine sets up the valid exit keys, calls a possible action procedure, then calls EditStringBuffer() until the user keys in a valid exit key, or keys in a valid value. To validate the field, the validate procedure is called, which checks that the string entered is of the right format, and within range. The format routine formats the string to be displayed in the HH:MM:SSXN form. The initialize routine is used set up a field in a form, and is called right after a call is made to InitField() when a form is being defined.

PROGRAM NAME: CEDARMM.EXE, ARRMAIN.EXE
MODULE NAME: CW_ADDEN.C
MAKE FILE NAME: CEDARRMM.MAK, ARRMAIN.MAK
LINK RESPONSE FILE: CEDARMM.LNK, ARRMAIN.LNK
DESCRIPTION

This module contains modified C-Worthy routines, and other additions. The first routine defined in here is InitUtilityNoHeader(). This is a copy of C-Worthy's InitUtility(), but has a couple of advantages. First, it does not display a three line header that the C-Worthy version does, allowing the whole screen to be used. Second, the display of the copyright is not performed, getting around the problem of having to blank out the copyright variables (a kludgie solution that Solution Systems had given us . . . I wonder why they call themselves "Solution" Systems?) The third advantage is that the variable screenSpeed is set to one, disabling the explosion of screens, which even though it is flashy, it wastes time.

The routine ChangeMessageLine() is defined here. It is a routine to display on any line, the current available keys for editing exiting, etc. A message number (a message defined with msglib in cedarmsg.mlc) is passed which corresponds to a sprintf format string. The other arguments correspond to the values to print as output using the format string. For example, say we want to display on line 24:

"Press <Esc> to return to the Main Menu"

We would define a message using msglib as:

BOTTOM_LINE_MSG—"Press <%s> to return to the Main Menu"

Then we could call the routine as follows:

ChangeMessageLine (25, RIGHT_JUSTIFY, BOTTOM_LINE_MSG, K_ESCAPE):

PROGRAM NAME: ARRMAIN.EXE
MODULE NAME: DOSGRAPH.C
MAKE FILE NAME: ARRMAIN.MAK
LINK RESPONSE FILE: ARRMAIN.LNK
MODULES IN THIS PROGRAM: ADCSUB1 ARRMAIN ATHMLIST BTIMEASC CEDARMSG CLIST CW_ADDEN CWBTIME DOSGRAPH FORMSHRT GETDEV INTERFAC VIEWSTSH
DESCRIPTION

The routine in the DOSGRAPH.C module are utility routines and user interace routines that service the HighC program ARRPROC.EXP. ARRPROC.EXP calls these routines by triggering a software interrupt (int 85).

The routine vectored to the interrupt calls the C routine int_dispatch() to dispatch the desired service. The assembly language routine intsetup(), defined in the module INTERFAC.ASM is called by the subroutine process() in ARRMAIN.C to set up the interrupt vector. A integer argument is passed from ARRPROC.EXP to int_dispatch() in the extended ax register. The module INTERFAC.ASM is assembly language that must be assembled in 386 real mode. This means that Intel 386 instruction op codes have to be generated. Information is also passed back to the ARRPROC.EXP program from dosgraph0(); The address of a structure is returned to int_dispatch(), which in turn passes it in "int_arg" to the interrupt routine to place in the extended ax register. The structure contains all the modifiable parameters for the "SCANNING" tuning features of CEDARS. These variables are first initialized to the values found in the file ARRPROC.INI. The may be later modified by calling the dosgraphs() routine.

The graphcall() subroutine is called by int_dispatch() the interrupt dispatch subroutine. The int_dispatch() routine passes the extended ax register value minus 10. This value determines the dosgraphN() routine number to execute: dosgraph0() thru dosgraph9().

The dosgraph0() routine is called by ARRPROC.EXP to perform initialization of the Real mode data structures. It calls the GetBoundaryMemory() routine defined in ADCSUB1.C. This is the first thing done, because we want to make such that there is enough contiguous memory to allocate for the analog to digital data conversion collection. The next routine it calls is init_cw_forms() which sets up the C-Worthy forms for dynamic variable modifications, for countscreen display, and for rythm list display. The routine the turns on graphics mode to draw the rate bars used in measuring in the user interface part of the system. And finally, it returns the address of the dynamic parameters structure, "plot_buf".

The dosgraph1() routine draws out the VGA/EGA graphics display area for the arrythmia that are going to be displayed in the color monitor.

The dosgraph2() routine calls stripGraphDisplay() to display a strip of digitized data at a specific offset. The buffer and number of points is passed in the plot_buf structure. The stripGraphDisplay() routine displays in EGA/VGA graphics on the color monitor.

The dosgraph3() routine uses a Microsoft graphics call to set the cursor. The row and col are passed to the routine by using the plot_buf structure.

The DrawRateBarImage() is the routine that is called to move the measurement bars in the EGA/VGA graphics screen. This routine is particularly touchy. It has been fixed and broken several times in the history of the project. DON'T MESS WITH IT!!!!

The dosgraph4() routine calls the DrawRateBarImage() routine. The row and col variables are passed using the plot_buf structure. The row variable is the initial X position of the rate bar. The col variable is the new X position where to place the bar. The bar is displayed using the GXOR attribute, that way the bar only needs to be drawn in both places, which has the effect of erasing the old, and displaying the new.

The SaveScreen() and RestoreScreen() routines are used to save and restore the C-Worthy screens. This is needed, since we swap between VGA/EGA color graphics and the C-Worthy EGA text display.

The read_parameters() routine reads in the "plot_but" structure parameters from the arrproc.ini file. See the "arrproc.doc" for details on the individual parameters. The routine used to read the tape.num file, and patient data file, but this has been suppressed, and they are now read in the HighC part of the system.

The routine init_cw_forms() calls the read_parameters() routine, and then creates the C-Worthy forms. It calls InitUtilityNoHeader() which is a C-Worthy look alike of the standard C-Worthy initialization routine that allows us to use the whole screen, and does not display the three line header. The routine sets up the fields for the parameter screen form, and finally creates the rythm comments list.

The init_on_count_form() routine sets up the count screen that is displayed during scanning to display the different arrythmias accumulators. Each accumulator has a boolean field that accompanies it that says whether the field is currently on "count", which means that the arrythmia once recognized, it is just simply counted and not stopped on. These fields' data is not allocated by C-Worthy, instead they correspond to the structure "form" in "plot_buf". The SaveScreen() calls at the end of this routine and at the end of init_cw_forms() doesn't really have any effect on the system. These are a couple of lines that may be removed, and the system will actually work the same.

All programs always have a bug.
All programs always have an extra line, that when taken out will not cause any ill effect.
Therefore, it follows that all programs may be reduced to one line that doesn't work.
Anonymous The dosgraph5() subroutine calls EditForm() on the parameter screen form. This routine when called from HighC by ARRPROC.EXP allows the user with the preset parameters from "arrproc.ini".

The dosgraph6() subroutine allows the user to select from the rythm comment list. From ARRPROC.EXP in "plot_buf.col" is passed the keystroke that the user hit (which is the first letter to one of the rythm comments). This key is placed in the C-Worthy virtual key buffer by calling UngetKey(). After the key is restored, SelectATHMlist() is called to actually display the list, and allow the user to select an element. The element number is passed back to ARRPROC.EXP by using the "plot_buf.row" variable.

The dosgraph7() subroutine used to allow interaction with the saved strips. This was disabled, because we ran out of memory. But with a little ingenuity this could be restored. Hint: use the linker's ability to allow overlays. Care should be taken not to allow this function execute while the digitize is going on. While in digitize mode, the buffer check routine must be called at least every 0.25 seconds. Setting up this form, and bringing up the overlay may take longer than that. Also, C-Worthy takes up ram while building a form, this also adds to the problem of running out of memory. See now why we didn't do it?

The dosgraph8() routine initializes the on count form, then allows the user to interact with it by calling the C-Worthy routine EditForm.

The dosgraph9() routine takes two separate courses depending on whether a scan is being performed on existing digitized data, or on a new tape that is currently being digitized. If it is for existing data, ADCInitDummyRead() is called to open the digitized file, and set the "plot_buf.BinFileSize" variable to the size of the file. Otherwise, ADCInit() is called to start the digitizing, and the data collection. InitBackgroundCheck() and EnableBackgroundProc() are called to begin the C-Worthy background routine that will check the buffer and save when required the digitized data to disk. This background check routine only works in the real mode program, and only while its routines are executing. This means that BackgroundCheck() needs to be called by the HighC program ARRPROC.EXP explicitly in intervals within 0.25 seconds from each other.

The dosgraph10() routine is used by ARRPROC.EXP to perform an explicit check on the digitize buffer. See above explanation on dosgraph9().

The dosgraph11() routine is called when a request is received from the Fox board for digitized data. This routine performs a BackgroundCheck() call before and after the FoxGetData() call to fill the Fox memory with data. See the discussion in ADCSUB1.DOC on how the data is placed in the Fox board memory.

The dosgraph12() routine gets digitized data for ARRPROC.EXP. The offset in the file to read is passed in the "plot_buf" structure, and the data is placed in the "plit_buf" structure. A BackgroundCheck() call is made before and after the data is read. This is to insure that not too much time has elapsed between digitized data saves. See the discussion on dosgraph9() above.

The testdorsgraph() routine was designed to allow ARRMAIN.EXE to run without running the Fox board and ARRPROC.EXP. This is mainly for testing of the screens, and timing buffer check gaps. See the ARRMAIN.DOC for an explanation on how to execute ARRMAIN without the other two programs also running.

PROGRAM NAME: CEDARMM.EXE
MODULE NAME: EDITS.C
MAKE FILE NAME: CEDARMM.MAK
LINK RESPONSE FILE: CEDARMM.LNK fifty of these fields, and each corresponds to one hour's worth of summarized data. The program TATABLES.C is responsible for summarizing the data that ARRPROC saved as the beat-by-beat file (BBB###.BIN). Each repeated data group in the General Table consists of ten data fields. These ten data fields correspond to each row in the displayable area.

The fields correspond to data fields and files as follows:

| FIELD # | DATA FILE | RECORD NAME | FIELD NAME | DESCRIPTION |
|---|---|---|---|---|
| 1 | GEN####.DAT | genHdr.gn_recs | [idx].gn_entry | SEQUENTIAL NUMBER |
| 2 | GEN####.DAT | genHdr.gn_recs | [idx].gn_end_time | HOURLY END TIME |
| 3 | GEN####.DAT | genHdr.gn_recs | [idx].gn_hr_lo | HOURLY LO HEART RATE |
| 4 | GEN####.DAT | genHdr.gn_recs | [idx].gn_hr_mean | HOURLY MEAN H. RATE |
| 5 | GEN####.DAT | genHdr.gn_recs | [idx].gn_hr_hi | HOURLY HI HEART RATE |
| 6 | GEN####.DAT | genHdr.gn_recs | [idx].gn_beats | HOURLY CNT OF H. BEATS |
| 7 | BRD####.DAT | brdHdr.br_recs | [idx].br_pauses | HOURLY CNT OF PAUSES |
| 8 | PCM####.DAT | pcmHdr.pm_recs | [idx].pm_beats | HRLY CNT OF PACED BTS. |
| 9 | SVE####.DAT | sveHdr.sv_recs | [idx].sve_total | SUPRAVENTRICULAR BTS. |
| 10 | VEN####.DAT | venHdr.vn_recs | [idx].vn_vpb_total | HOURLY VE BEATS. |

The routine genEdit() is called from MainMenuAction from within CEDARMM.C. The routine genEdit() first saves the current list, calls genForm to build the repeated data group field form. The C-Worthy routine Edit From() is called to allow the user to interact with the created form. When the user actually makes a change to one of the fields, only the screen data is modified. Not until the form is exited, are the data fields transferred to the summary data structure (i.e. genHdr.gn_recs ..., or venHdr.ven_recs ... ). The GenUpdate() routine is used for this purpose, and it is defined in the CEDARFLD.C module.

| MODULES IN THIS PROGRAM: | | | | |
|---|---|---|---|---|
| ATHMLIST.C | BTIMEASC.C | CLIST.C | CEDARFLD.C | CEDARMM.C |
| CEDARMSS.MLC | CW_ADDEN.C | CWBTIME.C | EDITS.C | FORM.C |
| FORMPROC.C | FREEFRM.C | FUNCSBIN.C | PATSCR.C | PICKLST.C |
| REPORT.C | RGROUP.C | RPTFORM.C | STRPINFO.C | VIEWSTRP.C |

DESCRIPTION

The screen that allow the editing of the summarize analysis are implemented in part in the EDITS.C module. EDITS.C are is where the C-Worthy Forms routines are called to build the screen fields, and also where the EditForm routine is called to allow the user to manipulate the fields.

The only forms currently implemented are The General Table, The Ventricular Ectopy Table, the Analyst Impressions form, and the Free from paragraph entry form.

The General Table is implemented using the routine genFrom() to build the fields to edit. The form consists of one repeated data group field. There may be up to The Ventricular Ectopy Table is also implemented using a C-Worthy form. The routine venForm() is used to build the fields to edit. The form consists of one repeated data group field just like the Generazl Table form. There may be up to fifty of these fields and each corresponds to one hour's worth of summarized data. The program TOTABLES.C is responsible for summarizing the data that ARRPROC saved as the beat-by-beat file (BBB###.BIN). Each repeated data group in the Ventricular Ectopy Table consists of twelve data fields. These twelve data fields correspond to each row in the displayable area. The fields corresponds to data fields and files as follows:

| FIELD # | DATA FILE | RECORD NAME | FIELD NAME | DESCRIPTION |
|---|---|---|---|---|
| 1 | VEN#####.DAT | venHdr.vn_recs | [idx].vn_entry | SEQUENTIAL NUMBER |
| 2 | GEN####.DAT | genHdr.gn_recs | [idx].gn_end_time | HOURLY END TIME |
| 3 | VEN####.DAT | venHdr.vn_recs | [idx].vn_vpb_tot | HOURLY VE TOTAL BEATS |
| 4 | VEN####.DAT | venHdr.vn_recs | [idx].vn_vpb_pair | HOURLY VE PAIRS CNT |
| 5 | VEN####.DAT | venHdr.vn_recs | [idx].vn_vbg_beat | HOURLY BIGEMINY BEATS |
| 6 | VEN####.DAT | venHdr.vn_recs | [idx].vn_vbg_evnt | HOURLY BIGEMINY EVENTS |
| 7 | VEN####.DAT | venHdr.vn_recs | [idx].vn_vtac_beat | HOURLY VTACH BEATS |
| 8 | VEN#####.DAT | venHdr.vn_recs | [idx].vn_vtac_evnt | HOURLY VTACK EVENTS |
| 9 | VEN#####.DAT | venHdr.vn_recs | [idx].vn_rt | HOURLY CNT OF R ON T |
| 10 | VEN####.DAT | venHdr.vn_recs | [idx].vn_ivr | HRLY CNT OF IVR BEATS |
| 11 | VEN#####.DAT | venHdr.vn_recs | [idx].vn_aivr | HRLY CNT OF AIVR BEATS |

The routine venEdit() is called from MainMenuAction from within CEDARMM.C. The routine venEdit() first saves the current list, calls genForm to build the repeated data group field form. The C-Worthy routine EditForm() is called to allow the user to interact with the created form. When the user actually makes a change to one of the fields, only the screen data is modified. Not until the form is exited, are the data fields transferred to the summary data structures (i.e. genHdr.gn_recs ..., or venHdr.vn_recs ... ). The VenUpdate() routine is used for this purpose, and it is defined in the CEDARFLD.C module.

The next form defined in EDITS.C, actually the first form displayed in the menu editing menu category, it strDisp(). This form originally was meant to be the strip header display and edit form. It has been modified to display and edit many other fields, and is now referred to as the Analyst Impressions form. This is probably the most complicated and fragile form in the system, so when making modifications to it, make sure you understand all the implications of the change. This includes moving fields around the screen, which could be hazardous since some of the validation or action routines are linked directly to the field position number. The Analyst Impressions screen is built in strForm(). This form is built entirely different than any other form in the system. Some of the field headers and prompts are created using lower level C-Worthy calls to ShowPortalLineAttribute so that complete control is maintained of where by are displayed. Besides all the fields that display maximums and minimums, and times of occurrance, the strip headers are displayed as a repeated data group field of the form. This repeated data group is defined in routine InitStripField() in the VIEWSTRIP.C module. All time fields in the Analyst impressions form use the validation procedure CreateStripValidate(). This routine sets up some parameters to pass to the routine viewstrp() in VIEWSTRIP.C. This routine will set up and display the strip from the digitized data stored at the tape time in VGA graphics mode. See VIEWSTRIP.DOC form more information on this routine. When the user exits the Analyst Impressions EditForm() routine, the data fields are recovered from the screen data areas, and then are saved.

PROGRAM NAME: CEDARMM.EXE
MODULE NAME: CEDARMM.C
MAKE FILE NAME: CEDARMM.MAK
 LINK RESPONSE FILE: CEDARRM.LNK

| MODULES IN THIS PROGRAM: | | | | |
|---|---|---|---|---|
| ATHMLIST.C | BTIMEASC.C | CLIST.C | CEDARFLD.C | CEDARMM.C |
| CEDARMSG.MLC | CW_ADDEN.C | CWBTIME.C | EDITS.C | FORM.C |
| FORMPROC.C | FREEFRM.C | FUNCSBIN.C | PATSCR.C | PICKLST.C |
| REPORT.C | RGROUP.C | RPTFORM.C | STRPINFO.C | VIEWSTRP.C |

DESCRIPTION

The FORMPROC.C module is a set of definitions. Here are defined the arrays that are used by C-Worthy as the function pointers to the routines that do the field specific work. The routines in the FormProcedure[] array of function pointers correspond to the routines in CEDARFLD.C. These are the Validate and Action procedures executed by C-Worthy routines like EditForm().

The AllocateProcedure[] array of function pointers are the C-Worthy field type routines that are called to allocate space of the specified field type. The order of these function pointers is very important, and it corresponds to the FORMPROC.H #define's. If a field is added, it should be added to the end of the array. If a field is deleted, all corresponding function pointers should be deleted in all other procedure arrays, and the FORMPROC.H file should be updated to correspond to the right array positions.

The DestroyProcedure[] array of function pointers are the C-Worthy field type routines that are called to deallocate space for the specified field type. See above for directions on how to add or delete a function.

The EditProcedure[] array of function pointers are the C-Worthy field type routines that are called to allow the user to edit the specified field type. See above for directions on how to add or delete a function.

The FormatProcedure[] array of function pointers are the C-Worthy field type routines that are called to set up the stiring field to display the the specified field type. See above for directions on how to add or delete a function.

The InitProcedure[] array of function pointers are the C-Worthy field type routines that are called to initialize the fields. These routines are called mainly from form creation routines, like patForm, genForm, etc.

PROGRAM NAME: ARRMAIN.EXE
MODULE NAME: FORMSHRT.C
MAKE FILE NAME: ARRMAIN.MAK
LINK RESPONSE FILE: ARRMAIN.LNK
 MODULES IN THIS PROGRAM: ADCSUB1 ARRMAIN ATHMLIST BTIMEASC CEDARMSG CLIST CW_ADDEN CWBTIME DOSGRAPH FORMSHRT GETDEV INTERFAC VIEWSTSH
 DESCRIPTION

The FORMSHRT.C module is a set of definitions. Here are defined the arrays that are used by C-Worthy as the function pointers to the routines that do the field specific work. The routines in the FormProcedure[] array of function pointers correspond to the routines in CEDARFLD.C. These are the Validate and Action procedure executed by C-Worthy routines like EditForm().

The AllocateProcedure[] array of function pointers are the C-Worthy field type routines that are called to allocate space for the specified field type. The order of these function pointers is very important, and it corresponds to the FORMSHRT.H #define's. If a field is added, it should be added to the end of the array. If a field is deleted, all corresponding function pointers should be deleted in all other procedure arrays, and the FORMSHRT.H file should be updated to correspond to the right array positions.

The DestroyProcedure[]array of function pointers are the C-Worthy field type routines that are called to deallocate space for the specified field type. See above for directions on how to add or delete a function.

The EditProcedure[] array of function pointers are the C-Worthy field type routines that are called to allow the user to edit the specified field type. See above for directions on how to add or delete a function.

The FormatProcedure[] array of function pointers are the C-Worthy field type routines that are called to set up the string field to display the the specified field type. See above for directions on how to add or delete a function.

The InitProcedure[] array of function points are the C-Worthy field type routines that are called to initialize the fields. These routines are called mainly from form creation routines, like patForm, genForm, etc.

PROGRAM NAME: CEDARMM.EXE/PRINTRPT.EXE
MODULE NAME: FREEFRM.C
MAKE FILE NAME: CEDARMM.MAK/PRINTRPT/MAK
LINK RESPONSE FILE: CEDARMM.LNK/PRINTRPT.LNK

DESCRIPTION

The FREEFRM.C module makes up the set of routines for editing the free form paragraph report. The parEdit() routine is the paragraph edit routine. All other related routines are called from it. This routine allocates the memory for the edit buffer, then reads or creates the edit file by calling read_par_File(). It uses the C-Worthy EditText() routine to perform the actual editing of the buffer.

PROGRAM NAME: CEDARMM.EXE, ARRPROCE.EXE, PRINTRPT.EXE, TOTABLE.EXE
MODULE NAME: FUNCSBIN.C
MAKE FILE NAME: CEDARMM.MAK, ARRPROC.MAK, PRINTRPT/MAK, TOTABLE.MAK
LINK RESPONSE FILE: CEDARMM.LNK, ARRPROCE.LNK, PRINTRPT.LNK, TOTABL.LNK

DESCRIPTION

The FUNCSBIN.C module is used by all other program in the CEDARS system. It's main function is to perform the input/output to/from the global data structures like patHdr, tapeHdr, genHdr etc. It also contains some supporting functions that are used in all or some of the programs.

The first five functions are compare functions for the array sorting done in TABLES.C.

The main set of routines follow the following pattern: A clear routine, that initializes the corresponding structure to some standard values. A read routine, that opens, reads from the file (The file name corresponding to the current log has been previously set by the routine SetFile()), and then closes the file. And, a write routine that opens, writes from the corresponding data structure, and closes the file.

All files are read and written in binary format, except for the "tape.num" file. This file is read using scanf() and written using fprintf().

PROGRAM NAME: ARRPROC.EXP, CEDARMM.EXE
MODULE NAME: GETDEV.C
MAKE FILE NAME: ARRPROC.MAK, CEDARMM.MAK
LINK RESPONSE FILE: ARRPROC.LNK, CEDARMM.LNK
DESCRIPTION

The GETDEV.C module reads the "devices.ini" file, and places the device information into the device_table[] array. Also, the graphics display position variables are initialized depending on the graphics device type. The second device in the table corresponds to the display device. It may contain a value of "4" for a EGA display, or a value of "5" for a VGA display. For more information on the specific devices and their values please refer to the file "devices.ini".

PROGRAM NAME: PRINTRPT.EXE
MODULE NAME: GREPSON.C
MAKE FILE NAME: PRINTRPT/MAK
LINK RESPONSE FILE: PRINTRPT.LNK

| MODULES IN THIS PROGRAM: | | | | | | |
|---|---|---|---|---|---|---|
| BTIMEASC | CEDARMSG | DELMAR | FREEFRM | FUNCSBIN | GREPSON | GRSTORE |
| HERSH | HUFFCALC | IGRAPH | KBINC | LASER_M | PRINTOPT | PRINTRPT |
| REPSUB | TEXTINFO | STRPINFO | | XONOFF | | |

DESCRIPTION

The module "grepson.c" is the set of routines that make up the "device independent" portion of the PRINTRPT.EXE program. In "grepson.h" are the data structure which is the starting point for the vectors to the data and functions that make up each device's routines. The data structure "device_specifications" is where we define resolution of the device, and all the routine addresses which are executed by the driving routines to output the desired text or graphics by a device.

The structure is defined below, with an explanation of each field:

```
struct    device_specifications
{
    long int      x_res;
    long int      y_res;
    int           passes;
    char          cmd_chr;
    void    (* or_current_point ) (void);
    void    (* xor_current_point ) (void);
    void    (* blank_current_point ) (void);
    void    (* draw_line) (int x1, int y1, int x2, int y2);
    void    (* move_draw_xy_array) ( int *buffer );
    void    (* abs_grid) ( long x1, long y1, long x2, long y2,
              int nx, int ny, int ex, int ey, int grid_type );
    void    (* dotline) ( int x1, int y1, int x2, int y2, int n);
    void    (* print_string) (char *string);
    void    (* print_char)(char c);
    void    (* init)(long xsize, long ysize);
    void    (* finish ) (void);
    void    (* color)( int color );
    void    (* vslew)( int num, int denom);
    void    (* vslew_set) ( int num, int denom);
    void    (* eject) (void);
    void    (* text_size) ( int size_code );
    void    (* device_startup)(void);
    void    (* device_germinate) (void);
};
```

'x_res' is the device's number of dots per inch on the x axis.
'y_res' is the device's number of dots per inch on the y axis.
'passes' is the number of passes the 'print head' is required to make to acheive the desired resolution.
'cmd_chr' is a single character used in the command string of some printers to specify print resolution.
'(# or_current_point) is a pointer to the 'OR' operation for a single pixel for the device currently in use.
'(# xor_current_point) is a pointer to the 'XOR' oepration for a pixel for the device currently in use.
'(# blank_current_point) is a pointer to the 'BLANK' operation for a pixel for the device currently in use.
(# init) ( ) is routine to initialized the graphics device driver.
(# finish) ( ) is routine to close or end output to device.
(# color) (int color) sets the printer color.

-continued (# eject) ( ) ejects a page on the device.
(# text_size) (int size_code) sets small, normal, or large text size.
    The size codes are defined in grepson.h
(# device_startup) ( ) primary init of device (initialization of
the device itself). See above for the init of the device driver
(# device_terminate) ( ) primary termination of device.

The instance 'defined_specs' of the type 'device_specifications' is now defined as a 4×3 array of 'device-specifications's. The first subscript indexes the type of printer currently defined. The current printer types available are the EPSON (subscript value 0), RICOH (subscript value 1), Laser Master (subscript value 3), and output as compressed data file (subscript value 3). The second subscript selects from the resolutions available for each defined printer, HIGH=2, MED=1, LOW=0. In the case of the LASERMASTER system (defined_specs[2][0 & 1 & 2]) which has only one available resolution (300 dpi) and requires no command character, the entries are duplicated in all three resolution columns.

The values to the structure are assigned in "grepson.c", and the actual function definitions for the EPSON type printers are defined in there also. The routines for the RICOH are the same as the ones of the EPSON. The routines for the Laser Master are defined in the module "laser_m.c.", and the routines for the compressed file are defined in "grstore.c".
PROGRAM NAME: PRINTRPT.EXE
MODULE NAME: GRSTORE.C
MAKE FILE NAME: PRINTRPT.MAK
LINK RESPONSE FILE: PRINTRPT.LNK The software interrupt is triggered by the protected mode program ARRPROC.EXP.

The interrupt is set up by using function 0×25 of the dos interrupt (0×21). The routine executed when the interrupt is triggered is the assembly routine "intdisp". It gets from the "eax" register the value that corresponds to the routine to call in the "C" module DOSGRAPH.C. It moves the value into the "C" variable "int_arg", and calls the "C" routine int_dispatch() in module ARRMAIN.C.

Upon return from int_dispatch() and whatever routines int_dispatch() calls, the value in "int_arg" is placed back onto "eax". This return value is the address of the "plot_buf" structure defined in the DOSGRAPH.C module.
PROGRAM NAME: CEDARMM.EXE
MODULE NAME: PATSCR.C
MAKE FILE NAME: CEDARMM.MAK
LINK RESPONSE FILE: CEDARMM.LNK

| MODULES IN THIS PROGRAM: | | | | |
|---|---|---|---|---|
| ATHMLIST.C | BTIMEASC.C | CLIST.C | CEDARFLD.C | CEDARMM.C |
| CEDARMSG.MLC | CW_ADDEN.C | CWBTIME.C | EDITS.C | FORM.C |
| FORMPROC.C | FREEFRM.C | FUNCSBIN.C | PATSCR.C | PICKLST.C |
| REPORT.C | RGROUP.C | RPTFORM.C | STRPINFO.C | VIEWSTRP.C |

DESCRIPTION

This module is a component of CEDARMM.EXE, and constitutes the screens for entering patient information (menu item #1 from category #1), and the diary data entry screens (menu item #2 from category #1). These screens are implemented using C-Worthy Forms library routines.

The routine patScr() is called from MainMenuAction() routine in module CEDARMM.C. This routine calls LogForm() to accept a log number, if the program CEDARMM was started with a default log number (C option on the command line) this number is displayed as a default in the LogForm. When a number is selected SetFile() is called to retrieve the data that corresponds

| MODULES IN THIS PROGRAM: | | | | | | |
|---|---|---|---|---|---|---|
| BTIMEASC | CEDARMSG | DELMAR | FREEFRM | FUNCSBIN | GREPSON | GRSTORE |
| HERSH | HUFFCALC | IGRAPH | KBINC | LASER_M | PRINTOPT | PRINTRPT |
| REPSUB | TEXTINFO | STRPINFO | | XONOFF | | |

DESCRIPTION

The "grstore.c" module contains the routines defined for storing a Holter scanner report in a format of compressed characters and graphics data onto a file. This allows reports to be transferred to a remote location or stored as an archive. The compression reduces amount of storage required and reduces the transmission time. The basic concept
PROGRAM NAME: ARRMAIN.EXE
MODULE NAME: INTERFAC.ASM
MAKE FILE NAME: ARRMAIN.MAK
LINK RESPONSE FILE: ARRMAIN.LNK
MODULES IN THIS PROGRAM: ADCSUB1 ARRMAIN ATHMLIST BTIMEASC CEDARMSG CLIST CW_ADDEN CWBTIME DOSGRAPH FORMSHRT INTERFAC VIEWSTSH
DESCRIPTION This little assembly language program has quite an important role in the CEDARS system. Its purpose is to set up an interrupt dispatch routine on interrupt 0×85.

to the log number. If a new log number is entered, new files are created for the number, and the global data fields are initialized. After the global data fields are set up, patScr() continues to build the screen for patient data entry.

The patients screen form is built using PatientForm(). It uses C-Worthy calls to initialize the form, create and initialize each individual field. patScr() calls PatientForm() to build the form, then it uses the C-Worthy routine EditForm to allow the user to interact with the form.

Each field in the data entry screen has a validation routine. Pointers to these routines are passed in at the time the fields are created in PatientForm(), as #define parameters. These #defines are defined in formproc.h, and represent an index value into structures defined in formproc.c. Pointers to routines are passed in the same manner for each field type, including a binary time field edit routine created by us. These routines include field type format, field type create, field type delete, field type edit, field type validate. Also there are action routines, that are executed when the edit routine first highlights the field, and validate routines that are executed when a valid exit key is pressed to leave the field. Of course not all fields use all the different procedures available to them, and these will be passed in as NOPROC.

PROGRAM NAME: CEDARMM.EXE
MODULE NAME: PICKLST.C
MAKE FILE NAME: CEDARMM.MAK
LINK RESPONSE FILE: CEDARMM.LNK

| MODULES IN THIS PROGRAM: | | | | |
|---|---|---|---|---|
| ATHMLIST.C | BTIMEASC.C | CLIST.C | CEDARFLD.C | CEDARMM.C |
| CEDARMSG.MLC | CW_ADDEN.C | CWBTIME.C | EDITS.C | FORM.C |
| FORMPROC.C | FREEFRM.C | FUNCSBIN.C | PATSCR.C | PICKLST.C |
| REPORT.C | RGROUP.C | RPTFORM.C | STRPINFO.C | VIEWSTRP.C |

DESCRIPTION

This module implements the patient selection screen (menu item #3 of category #1). This program allows the user to select from all available patient data on disk. It is implemented using a C-Worthy list. The list is created by opening all the PATNNNNN.DAT files, and retrieving the patient name, and dates, and appending them to a C-Worthy list. The list is then displayed, and the user is allowed to interact with it.

PROGRAM NAME: PRINTRPT.EXE
MODULE NAME: PRINTOPT.C
MAKE FILE NAME: PRINTRPT.MAK
LINK RESPONSE FILE: PRINTRPT.LNK

| MODULES IN THIS PROGRAM: | | | | | | |
|---|---|---|---|---|---|---|
| BTIMEASC | CEDARMSG | DELMAR | FREEFRM | FUNCSBIN | GREPSON | GRSTORE |
| HERSH | HUFFCALC | IGRAPH | KBINC | LASER_M | PRINTOPT | PRINTRPT |
| REPSUB | TEXTINFO | STRPINFO | | XONOFF | | |

DESCRIPTION

The module "printopt.c" contains the highest level routines for the printing or file storage of Holter scanner reports. The report selection routine and the individual table print-out routines are defined here. These routines have been designed to be device independent. The file "devices.ini" defines which printer type to use, or whether the reports are to be compressed and stored in a file. The "devices.ini" file is read in "printrpt.c.".

The first routine defined in this module is from where all other high level table print-out routines are called. This routine is "ReportSelection()", which works off of the selectionList[] array whoses elements' values are retrieved by the readNum() routine. These values are stored in the file "tape.num".

The next routine is CoverReport() which prints the first three pages of a report. The cover page, and the analyst impressions summary. This routine uses the print_string() routine to output text to the device. It uses the routines bigChar() and normChar() to set the size of the text to be output. It uses the routine center_print() to begin and end a section of text to be centered when output to the device. It also uses the LineOut() routine to output formated text to the device. This routine performs paragraph formatting, and returns the number of new lines added to the current page.

Other routines defined in "printopt.c" include: GenReport() which prints out the general table fields. This routine makes use of the routine TableHeader(), which is a generalized routine to print table headings when a new page starts. The routine makes use of the array header[] which is an array of character strings which is initialized a the beginning of the routine to the character strings which should be printed as table headings. The GenReport() routine also makes use of the routine TopLine() which prints at the top of the new page, the page number, and the report number (log number) and the patient name.

Other reports similar to GenReport() are VanReport(), BrdReport(), RnlReport(), and StpReport(). They all print out tabular data moved from the global data structures read in in the module "printrpt.c".

The other reports printed out from "printopt.c" require graphs to be printed. These graphics are drawn with proprietary routines defined in the modules "grepson.c", "grstore.c", "laser_m.c", "hersh.c", igraph.c", and "delmar.c". These routines make up a set of device independent routines, that allow the printing of graphics on four different devices; any Epson compatible printer, a Cannon laser printer, or to a compressed file used for transmission or archival. All graphics reports have similar format; all have local dimension variables, a viewport definition section, the data to be plotted is either retrieved from disk or calculated, routines are called to plot the data.

The report printing subroutines make use of the TopLine() subroutine, to print the same page header as the other report programs. They also make use of set_linestyle() subroutines to set the graphics mode, normChar() to set ext mode. They use BtimeAsc() to convert from "long int" time to ASCII time. For actual graphics plotting, the routine igr_open() is used to set the chosen device resolution (LOW, MED, HIGH), to call the used device specific init routine, and to get set up the stroked text font by calling getfont(). The text font used for this system is hershey font (see the documentation for "textinfo.c"). The routine set_worldmapping() is called to set up the global world coordinates. These are variables that determine the boundaries of where data is actually plotted; upper right hand corner of plot space (x,y) coordinates, lower left hand corner (x,y) coordinates, and clipping region variables. The routine set_world_inch_mapping() routine takes parameters that are defined in inches, and makes conversions to pixels before calling the set_world_mapping() routine. The world_grid() routine is called to set up a grid background for the plot space. The world_grid() routines calls map_w_d() routine which maps world coordinates to device coordinates, and then calls the abs_grid() routine. The abs_grid() routine calls the device specific abs_grid() routine. Graphs can be printed with big grids, continuous small grids, small grids with big spaced crossed, or no grids at all. Also, all grid types may have a box drawn around them.

One the plot space has been prepared, the plotting buffer is filled with the data to be plotted. The plotting buffer is a one dimensional array which contains the Y-coordinate data. The X-coordinate is usally time, and its increment is determined by the number of points to plot in the currently defined world. The worl_plot_array() routine is then called to do the graphing. This routine graphs the data into an array in RAM, and then copies that plot space to the outbuff[][] array using the device defined routine to do the plotting. Finally, the routine igr_close() is called to perform the device specific finish() routine. The finsh() routine is used to call the device independent routine to move the outbuf[][] array to the print device.

Other routines used to perform graphics operations are: world_draw(), which converts data to device coordinates, and calls the absolute device routine to draw a clipped line from the previously set x and y coordinates. The world_move() routine moves the current (x,y) coordinates to a new (x,y) coordinate. The map_w_d() routine is called within it to translate the world coordinates to device coordinates. The routine draw_just _test() is used to draw a text string onto the plot space. This routine calls map_w_d() to map the world coordinates to device coordinates, then is calls stringwidth() to determine the ture width in inches of the text string. Then it calls draw_abs_text() which calls the do_stroke() routine for each character in the string. The world_dotline() routine is called to draw a dotted line. It does the same world to device coordinates translation, and then calls the device specific dotline() routine. The world_clipped_line() routine is a short way of calling world_move(), and then calling world_draw(). The routine world_bar_draw() is a routine to draw a single bar in a bar chart. It allows for shading by drawing equally spaced lines through out the bar.

A generalized routine is available to label the graphed reports. The text is printed using the stroked graphics characters, this allows for the printing to occur within the graphics of the charts, strips etc. The routine is graph_labels(), and is defined in "printopt.c". It labels the axis, and makes the tick marks on the axis.

PROGRAM NAME: PRINTRPT.EXE
MODULE NAME: PRINTRPT.C
MAKE FILE NAME: PRINTRPT.MAK
LINK RESPONSE FILE: PRINTRPT.LNK printer, or an Epson graphics or compatible printer. Also the program will print the report in a compressed format to a file, which in turn may be transmitted to a remote sit, and then printed. The source code is semi-structured, the other device drives could be implemented. The PRINTRPT.EXE program is also used right after the scanning portion of the system. At this point the only printing done is that of eight second printscreens of strips.

The "printrpt.c" module contains the mainline of the program. Here we open the data files, and fill the global data structures with the data from the analysis. Only a portion of the opening of files is done if the program is being used to print the "print screens" of strips, this is because some files have not been created yet. The program is driven by flags set on or off in the "tape.num" file. The first of these flags checked is the CAPTURE_REPORT flag which determines whether the report will be printed, or compressed and put into a file. The fiel menu for the compressed report is passed in the tapeHdr structure. To select the device of output the igr_select() routine is called. The routine where the reports are selected for printing, ReportSelection(), is then called. This routine is in the module "printopt.c".

PROGRAM NAME: CEDARMM.EXE
MODULE NAME: REPORT.C
MAKE FILE NAME: CEDARMM.MAK
LINK RESPONSE FILE: CEDARMM.LNK

| MODULES IN THIS PROGRAM: | | | | |
|---|---|---|---|---|
| ATHMLIST.C | BTIMEASC.C | CLIST.C | CEDARFLD.C | CEDARMM.C |
| CEDARMSG.MLC | CW_ADDEN.C | CWBTIME.C | EDITS.C | FORM.C |
| FORMPROC.C | FREEFRM.C | FUNCSBIN.C | PATSCR.C | PICKLST.C |
| REPORT.C | RGROUP.C | RPTFORM.C | STRPINFO.C | VIEWSTRP.C |

DESCRIPTION

The REPORT.C module along with RPTFORM.C and CEDARFLD.C as supporting modules make up the printing main menu selections. The subroutines ReportSelection1() thru ReportSelection6() are called from subroutine MainMenuAction() in CEDARMM.C. These routines set up the print flags to display using the report form, and the flags that are written out in the tape.num file. Then these flags are read in the PRINT.EXE program to actually print the report. The print program was made a separate program because it is device independent code which made the program too big. Also it was hoped that in the future this print program may run independently and concurrently with scanning (That's when we get a Intel 80586 running SuperConcurrentDos).

ReportSelection1() is the first menu sub-item of the print menu. It calls miscscr() which allows the user to type in a report header.

PrintIt() is the subroutine that is called from all other

| MODULES IN THIS PROGRAM: | | | | | | |
|---|---|---|---|---|---|---|
| BTIMEASC | CEDARMSG | DELMAR | FREEFRM | FUNCSBIN | GREPSON | GRSTORE |
| HERSH | HUFFCALC | IGRAPH | KBINC | LASER_M | PRINTOPT | PRINTRPT |
| REPSUB | TEXTINFO | STRPINFO | | XONOFF | | |

DESCRIPTION

The PRINTRPT.EXE program is the set of routines responsible for the actual printing of the reports the rest of the system has created. PRINTRPT.EXE will actually allow printing to any device according to the "devices.ini", but currently only supports a laser ReportSelectionN() subroutines. It is the routine that brings up a little pop-up menu to allow the user to select whether he wants to print a report, or to transmit it using ProComm. When a section is make, the subroutine PrintNmae() is called to set the last few flags. If either printing or transmitting were selected from the pop-up menu, the program exits after writing the tapeHdr record to the tape.num file. The program exits to the RUN.EXE program that starts the print program if printing was selected. The program creates the "SEND.CMD" file for sending a report using Procomm, and exits with another exit code to RUN.EXE, so that RUN.EXE knows to start Procomm after it runs the print program. The last selection from from the pop-up menu allows that a standard report be modified to more accurately define which parts of the report should be printed or not printed. This part of the routine calls rptForm() in RPTFORM.C. This subroutine builds the form that allows changes to the flag settings for the print program, and allows change to the name of the compressed transfer file created by the print program.

PROGRAM NAME: CEDARMM.EXE
MODULE NAME: RGROUP.C
MAKE FILE NAME: CEDARMM.MAK
LINK RESPONSE FILE: CEDARMM.LNK

| MODULES IN THIS PROGRAM: | | | | |
|---|---|---|---|---|
| ATHMLIST.C | BTIMEASC.C | CLIST.C | CEDARFLD.C | CEDARMM.C |
| CEDARMSG.MLC | CW_ADDEN.C | CWBTIME.C | EDITS.C | FORM.C |
| FORMPROC.C | FREEFRM.C | FUNCSBIN.C | PATSCR.C | PICKLST.C |
| REPORT.C | RGROUP.C | RPTFORM.C | STRPINFO.C | VIEWSTRP.C |

DESCRIPTION

The RGROUP.C module is the source code for repeated data groups routines supplied with the C-Worthy libraries. The reason this code is compiled and linked with the CEDARMM.OBJ's is that the routine MoveInsideRepeatedGroup() has been redefined to be a globally accessible routine, instead of static. This modification was done when C-Worthy was upgraded from version 0.988 to version 1.0.

PROGRAM NAME: CEDARMM.EXE
MODULE NAME: RPTFORM.C
MAKE FILE NAME: CEDARMM.MAK
LINK RESPONSE FILE: CEDARMM.LNK

| MODULES IN THIS PROGRAM: | | | | |
|---|---|---|---|---|
| ATHMLIST.C | BTIMEASC.C | CLIST.C | CEDARFLD.C | CEDARMM.C |
| CEDARMSS.MLC | CW_ADDEN.C | CWBTIME.C | EDITS.C | FORM.C |
| FORMPROC.C | FREEFRM.C | FUNCSBIN.C | PATSCR.C | PICKLST.C |
| REPORT.C | RGROUP.C | RPTFORM.C | STRPINFO.C | VIEWSTRP.C |

DESCRIPTION

The REPORT.C module along with RPTFORM.C and CEDARFLD.C as supporting modules make up the printing main menu selections. RPTFORM.C is the module where the rptForm() subroutine is defined. This form allows changes to the print flags and to the file name used to transmit a file. The transmit file name also has the name "capture file", this is because the name comes from "the old days" when a file to be transmitted was captured using a PC from the Cardio Data MK4's print port. The following is an example how all the form calling program should do it:

```
ReportSelection##()
{
    FORM *editForm,*rptForm();
    int errorCode;
    char printStr[PRINT_OPTIONS_MAX];
/**** make assignments to printstr here ****/
```

-continued

```
    PushList();
    InitList();
    editForm = rptForm(printStr);
    errorCode = EditForm(editForm, FC_NO_FLAGS,
    NOPROC);
    DestroyForm(editForm);
    PopList();
    writeNum();
    return(0);
}
```

IMPORTANT: Care should be taken when fields are added, or deleted. The field numbers correspond to the position in the print flags array (Yes we know . . . Bad design. But, when people want things a week ago yesterday you tend to do things the fastest way possible without totally shooting yourself in the foot). The other places that would need change if a field was deleted or modified, would be the PrintName() subroutine in REPORT.c, it copies the flags to the tapeHdr structure. Also The PRINTOPT.C module would request modifications.

The first field of the form is the transmit file name, and has a validate procedure that is executed after the field is changed. The validate routine is CaptureName() which lives in CEDARFLD.C. It is responsible copying the name into the tapeHdr structure.

PROGRAM NAME: RUN.EXE
MODULE NAME: RUN.C
MAKE FILE NAME: RUN.MAK
LINK RESPONSE FILE: RUN.LNK
MODULE IN THIS PROGRAM: NONE
DESCRIPTION

This program is the conductor of the CEDARS (alias Century Color Trace) System. It was created, because the entire system is not large enough to fit in RAM at the same time, and there are programs compiled with different C compilers that execute from here. The first program to execute, is cedarmm. This program is executed after every major step of the analysis process. When a menu item is selected in cedarmm that requires one of these other programs to execute, cedarmm is exited with an error code greater than 200. For example, when digitizing of a new tap is requested by the user, cedarmm is exited with 201 or 205 for CASSETTE digitizing, or REEL TO REEL digitizing. Then run will execute "frun" with is the FORTH language loader, which loads the FORTH scanning portion of the scanner. As soon as that program exits arrmain is executed. Arrmain is the user interface portion of the scanner. When the tape is digitized and scanned (this happens simultaneously, see the arrmain.C documentation for further explanations on how this is accomplished(, the totable program is executed to do the data reduction to an hourly basis from the beat by beat file. When totable is complete, cedarmm is started again, this time with a continuation flag, so that the current patient's data is loaded. This will allow the user to select one of the editing menus without having to load a patient from the patient directory.

PROGRAM NAME: CEDARMM.EXE/PRINTRPT.EXE/ARRMAIN.EXE
MODULE NAME: CEDARMM.C
MAKE FILE NAME: CEDARMM.MAK/PRINTRPT.MAK/ARRMAIN.MAK
LINK RESPONSE FILE: CEDARMM.LNK/PRINTRPT.LNK/ARRMAIN.MAK
DESCRIPTION

The module STRIPINFO.C contains only one subroutine, strpInfo(). It is the routine that puts together the string for the top line display of the strips that are displayed or printed. C E N T U R Y C O L O R T R A C E.

Processor Hardware

The system comprises an IBM compatible microcomputer with an Intel 80386 microprocessor. It has 2 MB of RAM and a RAM cache disk controller with an average access time of under 1.0 msec. with a standard Seagate ST250 80 Megabyte hard disk drive. A second on board computer is used to perform high speed analysis and calculations; this is a SC/FOX board from Silicon Composers, Inc. The board uses a Harris RTX-2000 microprocessor, which is a 16 bit stack oriented process that implements the FORTH language almost directly. The processor runs at about 8 to 10 million instructions per second according to Silicon Composers, Inc. specifications. A second third party board is used to implement a proprietary analog to digital and digital to analog conversion board. The board used is a PDMA-32 from Metrabyte Corporation, which allows the A/D and D/A to make use of the on board DMA chip to make direct memory transfers without the aid of the Intel 80386.

Display Hardware

The system uses two separate displays to give maximum flexibility and speed. The system editing, reporting, and main user interface functions are implemented using a multi-syn color graphics display driven by a Vector Graphics Array (VGA) compatible card. This gives a pleasant high resolution color graphics display that is not strain producing to the analyst. The superimposition, and most commonly used display sequence have been implemented on the Vector display. The vector display is driven by the proprietary A/D and D/A board, which gets its data directly from RAM which is placed there by the SC/FOX FORTH board.

Hardcopy Hardway p The system has been designed to be device independent where possible, and this includes the printer device. The system currently implements printing on Epson compatible graphics printers, and xxxxx laser printer. The printing speed on the laser printer is enhanced by a Laser Master board that transmits an image to the laser printer instead of digit data.

SOFTWARE COMPONENTS

The software that implements the Century Colortrace is divided into Four main logical components: Analog Data Conversion and Collection, Data Analysis Phase, Data Reduction Phase. Patient Data Entry and Analysis Editing, and Report Printing and Digital Data Transmission. These different logical modules of the system have been implemented using Two different "C" language compilers, and the FORTH language on an on board co-processor. All operating system specific applications have been coded in Microsoft "C", with C-Worthy screen management libraries from Solution Systems. All scanning analysis related applications have been coded in High-C a real mode 32-bit "C" compiler from Metaware Inc.

Analog Data Conversion and Collection

Analog data conversion is driven by a Microsoft "C" program that is started by the Data Analysis Phase program, and runs concurrently with the analysis. The program has routines that start and stop the tape drives, start and stop the data conversions, and start and stop the DMA controller. The main data collection loop implements a multi-buffering scheme to ensure that not data overflow occurs during data conversion and collection. The routine that checks the buffers is called at controlled intervals as a background task of the C-Worthy interface library when the system operates in protected mode, and a background routine of the Data Analysis Phase program when the system operates in real mode. The background check routine shares access to the hard disk, where digitized data is saved until the next tape is digitized with the display fetch data routines. These shared access I/O transactions are carefully synchronized.

Data Analysis Phase

The Data Analysis Phase is implemented in High-C from Metaware Inc., which executes in Intel 80386 real mode. The runtime unit is a protected mode runtime manufactured by PharLap Inc. The High-C code is spawned from a Microsoft shell program that sets up an interrupt dispatcher to allow communication between the High-C program and the protected mode program where Microsoft DOS services are performed for the High-C program. The High-C Data Analysis Phase Program implements the following features in a large processing loop:

Manufacturing an interface with the SC/FOX board to keep its pipeline feed with digitized data, where the SC/FOX board perform the R-peak finding.

Maintains an interface with the SC/FOX board to keep it displaying the digitized data on the Vector display.

Call routines to perform template matching to classify the current beat.

Calls routines to classify the current complex. To do this a Non-deterministic state machine algorithm has been identified. This algorithm is enhanced with most likely to occur weighted priorities for each complex.

For each unrecognized template, a user interface routine is called to identify it.

Also a user interface routine is called to allow the analyst to modify analysis parameters, allow the analyst to perform strip labeling and saving, strip measurements, and backwards scanning. This user interface routine is called at the analysts request, or when a new complex has been identified.

Also, as scanning progresses, a history file is saved with information about each beat. This file is later used in the Data Reduction Phase to identify Maximum/Minimum heart rates, ST Elevation/Depression maximums, Maximum Pauses Maximum VTACH, Minimum Bradycardia rhythms. etc.

Data Reduction Phase

This module of the system is executed after the analysis has been performed, and was designed to off-load some of the processing burden as a batch step. These set of routines were written in Microsoft "C", and are executed by the integrator module as a sequential step after the Analysis Phase. This part of the system, calculates maximums and minimums, it places counts in the different system data structures. It ranks different run types, along with pauses, and ST trent analysis. It places all the reduced data into data structures readable by the Analyst Editing functions.

Patient Data Entry and Analyst Editing Functions

These set of routines are the second most important interface with the analyst. They allow the analyst to maintain a database of reports, and allow the data entry of patient and diary information. At the end of scanning a tape, the analyst uses the same module to "edit" the collected statistics. The analysts at the end of the analysis may view strips saved during the analysis phase, and may also look at new strips displayable in the color graphics display. The analyst at this point may save the top ranked heart rate strips. VTACH strips, Brady strips, and ST Elevation and Depression strips.

Report Printing And Digital Data Transmission

Using simple menu selections from the displayed menu the analyst may selecting printing of transmission of reports to remote printers or data receivers. The report printing is implemented using custom high speed algorithms that are device independent. These are coded in Microsoft "C", and run as a separate module spawned from the integrator module. The data transmission is accomplished by spawning the communications program ProComm form DataStorm Technologies with a scrip file.

| Real Time Clocks: | |
|---|---|
| Signal Inputs: | |
| Time-encoded Tapes: | Timing track used for digital time precision. |
| Reel Tapes: | Optical Encoder on capstan. |
| Time Format: | 12 hours, AM or PM, Day 1 or 2 |
| Vector Display: | |
| CRT Size: | 19 inch (diagonal) |
| Electronic Cursor: | 2 seconds (1 or 2 beats) displayed for each channel. |
| ECG Sensitivity: | nominal 10 grid units/mv (slightly larger than 1 mm grid, calibrated to screen grid template) |
| ECG Sample Rate: | 200 Samples/sec |
| Resolution: | 8 bits companded |
| Digital Data and Strip Display: | |
| CRT Size: | 13 inch (diagonal) |
| Display Format: | 640 × 480, 16 color graphics and text |
| Display Modes: | Strip (8 seconds each channel) Arrhythmia Counts Parameter update screens |
| Strip Display: | 8 seconds for each channel, 25 mm/sec. |
| ECG Sensitivity: | nominal 10 mm/mV |
| Disk and Computer System: | IBM AT compatible, 80386 25 Mhz processor |
| RAM Memory: | 4 Megabyte (total) |

-continued

| | |
|---|---|
| Floppy Drive: | 1.2 Meg 5.25 in., 3690KB 5.25, or 1.4 Meg 3.5 in. |
| Operating System: | MS DOS 3.3 |
| Winchester Hard Drive: | 80 MB |
| xxxxx Hard Disk controller | |

PROGRAM NAME: CEDARMM.EXE
MODULE NAME: CEDARMM.C
MAKE FILE NAME: CEDARMM.MAK
LINK RESPONSE FILE: CEDARMM.LNK

| MODULES IN THIS PROGRAM: | | | | |
|---|---|---|---|---|
| ATHMLIST.C | BTIMEASC.C | CLIST.C | CEDARFLD.C | CEDARMM.C |
| CEDARMSG.MLC | CW_ADDEN.C | CWBTIME.C | EDITS.C | FORM.C |
| FORMPROC.C | FREEFRM.C | FUNCSBIN.C | PATSCR.C | PICKLST.C |
| REPORT.C | RGROUP.C | RPTFORM.C | STRPINFO.C | VIEWSTRP.C |

DESCRIPTION

The module VIEWTRIP.C makes up the routines that retrieve and display binary data into strips of heart beats. These routines are called mainly through strEdit() and its action and validation routines. The strEdit() routine is the analyst impressions form.

The basic routines that allow the display of binary data are DispStrips(), and stripGraphDisp(). These routines take as parameters an expanded binary data buffer, number of points to display, and the highlight color for the beat in the middle of the display. This is the way that strips are stored when they are saved during scanning, and when they are saved through the analyst impressions screen.

The stripGraphDisp() is the routine that actually displays the strip on a VGA or EGA color graphics screen. The coordinates are assigned in the routine init_devices() in GETDEV.C according to the device indicated in devices.ini. The graphics routines used are the standard Microsoft C runtime library routines.

The DispStrips() routine calls stripGraphDisp() and displays the topline heading passed in as a character string. DisplStrips() is called by the saved strips display routine viewStrip(), as well as by the save new strip routine ViewNewStrip().

The routine viewStrips() is the routine called to perform the display of a specific saved strip. This is called from the validate procedure of any of the time fields in the strips' repeated group of the analyst impression form. The viewStrips() routine takes a strip number as one of its parameters, which corresponds to the relative strip number in the saved strip binary file. The routine opens the strip file, allocates a buffer, seeks to the correct position, reads the data into the buffer, and then calls DispStrips() to do the display.

The GetStripData() routine retrieves from the digitized data file, as opposed to the strip binary file. It accepts a time value that corresponds to a true time during the recording of the tape. This time is converted to an offset, and the data read from "data.bin". The data is then expanded, and placed in the caller supplied buffer. GetStripData() is called by ViewNewStrip() routine.

The NullCreateNewStripValidate() routine is like one of those pages in a book or manuscript that say "THIS PAGE INTENTIONALLY LEFT BLANK".

The InitStripData() routine adds data to the repeated data group part of the analyst impressiones form defined in InitStripField(). It takes the data from the global structures strHdr and frmHdr, and places it in the defined repeated data group.

InitStripField() defines three new fields to the analyst impressions form. It is a routine that is defined much like the routine defined in EDIT.C. This one is called by strForm() to create the Total Saved Strips field, the time for inserting a new strip field, and the repeated data group for the strip information display.

The SaveNewStrip() routine inserts a new strip repeated data group element at the appropriate time in the current repeated data group elements. It updates the current form variables. The routine also updates the global strHdr and frmHdr structures with the new addition. Towards the end of the routine, it calls the UpdateStripCount() routine to add to the repeated data group count, and two global variables are set to the current repeated data group element. The variables are used by the action procedure of the strip repeated data group. This action procedure will get performed when the form edit takes control again, and sees that the current field to display and edit is the repeated data group field.

The ViewNewStrip() routine is the validate routine for several of the time fields in the analyst impressions routine. This routine does a log of processing depending on the field number that executed it. For several of the fields which had a top ten array created in the TOTABLES.C module, the digitized data is displayed as strips for the user to view, and decide whether the current top element is the correct strip to have as the top for the category.

The first thing the routine does is to make sure that the binary data in "∓data.bin" corresponds to the current log number's data structures currently being analyzed. Then depending on the field number of topTen and indx variables are assigned. After the field dependent assignments are made, the routine loops until the user either saves a strip, by pressing the """" key, or exits by pressing escape. The user may mark top ten elements as delected to place another as the true top ten element. If the top ten ranking is changed, the global data structure that corresponds to the field is updated.

PROGRAM NAME: ARRMAIN.EXE
MODULE NAME: VIEWSTSH.C
MAKE FILE NAME: ARRAMIN.MAK
LINK RESPONSE FILE: ARRMAIN.LNK

| MODULES IN THIS PROGRAM: | | | | | |
|---|---|---|---|---|---|
| ADCSUB1 | ARRMAIN | ATHMLIST | BTIMEASC | CEDARMSG | CLIST |
| CW_ADDEN | CWBTIME | DOSGRAPH | FORMSHRT | | |
| INTERFAC | VIEWSTSH | | | | |

DESCRIPTION

The VIEWSTSH.C module is an ancestor of the VIEWSTRP.C routine. This set of routines are responsible for the display of expanded digitized binary data as strips on a VGA or EGA display. The coordinates used in stripGraphDisp() are assigned in the routine init_devices in module GETDEV.C. When ARRPROC.EXP makes a request to display on the color graphics display, the interrupt dispatcher calls dosgraph2() which calls stripGraphDisp().

What is claimed is:

1. A system used by a technician for evaluating a Holter ECG tape having a signal representing a series of waveforms thereon and for generating a report reflecting the evaluation, said system comprising:

means for generating from the ECG tape an analog signal representative of the ECG waveforms recorded on the tape;

means for converting the analog signal into a digital signal, said means for converting includes an A/D converter providing at least two channels of 12 bit digital signal data corresponding to the analog signal and a ROM having a logarithmic look-up table therein for converting each channel of the 12 bit digital signal to an 8 bit digital signal;

computing means including a data bus, a random access memory for storing the digital signal, a processor for controlling the operation of the system and for computing from the digital signal waveforms representing the ECG;

means for displaying the waveforms representing the ECG;

a storage device connected to the data bus;

direct memory access means for moving the 16 bit digital signal data from the converting means to the storage device random access memory as an intermediate step for storing the digital signal in the storage device, the two 8 bit digital signals being processed simultaneously by the direct memory access means as 16 bit digital signal data;

whereby the resolution of low magnitude digital signals is substantially preserved while larger magnitude digital signals are represented with fewer bits.

2. The system of claim 1 wherein the computing means comprises a personal computer.

3. The system of claim 1 further comprising a co-processor including means for moving data from the storage device for analysis by said processor.

4. The system of claim 1 wherein said computing means includes means for matching of waveforms defined by the digital signals stored in the storage device to waveforms as defined by the technician.

5. The system of claim 4 wherein the matching means determines a difference between the value at various points of a waveform being evaluated and the value at corresponding points of each template in a sequential order and wherein the matching means defines a match as the lowest sum of the absolute values of each of the differences within a preset range.

6. The system of claim 5 wherein the sequential order is determined by placing at the beginning of a queue the last template which has been matched and wherein the waveform being evaluated is compared to templates in the queue starting with the template at the beginning of the queue.

7. The system of claim 6 wherein the matching means determines a minimum template difference for each template which corresponds to the minimum of the sums of the absolute value of the differences between the value at various points of the template and the value at corresponding points of another template of a different category and wherein the comparison is discontinued when a match is found and the minimum template difference between the matched template and every other template of a different category is more than twice the difference between the waveform being evaluated and the matched template.

8. The system of claim 1 wherein said computing means includes means for analyzing the series of waveforms according to a nondeterministic logic state analysis.

9. The system of claim 8 wherein the analyzing means indicates when the series of waveforms correspond to ventricular ectopy (VE), bigeminy, VE pair and ventricular tachicardia.

10. The system of claim 1 wherein said computing means includes means for identifying R waveforms within the series, means for comparing peak waveforms to a T waveform template and means for indicating when a peak waveform matches a T waveform template.

11. The system of claim 1 wherein said computing means includes means for generating a full disclosure file representing the series of waveforms on the tape, said file comprising compressed data of limited resolution and limited sampling rate.

12. The system of claim 11 wherein said compressed data comprises a selected number of a previous sample subtracted from a subsequent sample.

13. The system of claim 12 wherein said compressed data is further compressed by a compression technique selected from run length and Huffman techniques.

14. The system of claim 1 further comprising means responsive to the technician for identifying periods during which only template matches are identified.

15. The system of claim 1 further comprising means for providing two channels DMA processing by combining two 8 bit channels to form 16 bit words.

16. A system used by a technician for evaluating a Holter ECG tape having a signal representing a series of waveforms thereon and for generating a report reflecting the evaluation, said system comprising:
  means for generating from the ECG tape a digital signal representative of the ECG waveforms recorded on the tape;
  computing means including a data bus, a memory for storing the digital signal, and a processor for controlling the operation of the system and for evaluating the digital signal to provide waveforms representing the ECG;
  means for displaying the waveforms representing the ECG;
  a storage device connected to the data bus;
  means for moving the digital signals from the generating means to the storage device for storing the signals in the storage device; and
  wherein the processor evaluates the signals at a rate independent of a rate at which the means for moving moves the digital signal from the generating means to the storage device.

17. The system of claim 16 further comprising means for converting including a converter providing at least a 12 bit digital signal corresponding to the signal and a ROM having a logarithmic look-up table therein for converting the 12 bit digital signal to an 8 bit digital signal whereby the resolution of low magnitude digital signals is substantially preserved while larger magnitude digital signals are represented with fewer bits.

18. A system used by a technician for evaluating a Holter ECG tape having a signal representing a series of waveforms thereon and for generating a report reflecting the evaluation, said system comprising:
  means for generating from the ECG tape a digital signal representative of the ECG waveforms recorded on the tape;
  computing means including a data bus, a memory for storing the digital signal, and a processor for controlling the operation of the system and for computing from the digital signal waveforms representing the ECG;
  means for displaying the waveforms representing the ECG;
  a storage device connected to the data bus;
  means for storing the digital signal in the storage device; and
  matching means for determining a difference between the value at various points of the waveform being and the value at corresponding points of templates in a sequential order and wherein the matching means defines a match as the lowest sum of the absolute values of each of the differences within a preset range.

19. The system of claim 18 wherein the sequential order is determined by placing at the beginning of a queue the last template which has been matched and wherein the waveform being evaluated is compared to templates in the queue starting with the template at the beginning of the queue.

20. The system of claim 19 wherein the matching means determines a minimum template difference for each template which corresponds to the minimum of the sums of the absolute value of the differences between the value at various points of the template and the value at corresponding points of another template of a different category and wherein the comparison is discontinued when a match is found and the minimum template difference between the matched template and every other template of a different category is more than twice the difference between the waveform being evaluated and the matched template.

21. A system used by a technician for evaluating a Holter ECG tape having a signal representing a series of waveforms thereon and for generating a report reflecting the evaluation, said system comprising:
  means for generating from the ECG tape a digital signal representative of the ECG waveforms recorded on the tape;
  computing means including a data bus, a memory for storing the digital signal, and a processor for controlling the operation of the system and for computing from the digital signal waveforms representing the ECG;
  means for displaying waveforms representing the ECG;
  a storage device connected to the data bus;
  means for storing the digital signal in the storage device; and
  wherein said computing means includes means for analyzing the series of waveforms according to a nondeterministic logic state analysis.

22. The system of claim 21 wherein the analyzing means indicates when the series of waveforms correspond to ventricular ectopics (VE), bigeminy, VE pair and ventricular tachicardia.

23. The system of claim 21 wherein said computing means includes means for identifying R waveforms within the series, means for comparing peak waveforms to a T waveform template and means for indicating when a peak waveform matches the T waveform template.

24. The system of claim 21 wherein said computing means includes means for generating a full disclosure file representing the series of waveforms on the tape, said file comprising compressed data, of limited resolution and limited sampling rate.

25. The system of claim 21 further comprising means responsive to the technician for identifying periods during which only template matches are identified.

* * * * *